US009572877B2

(12) United States Patent
Cho et al.

(10) Patent No.: US 9,572,877 B2
(45) Date of Patent: Feb. 21, 2017

(54) VACCINE FOR INDUCING AN IMPROVED IMMUNE REACTION

(75) Inventors: Yang Je Cho, Seoul (KR); Na Gyong Lee, Seoul (KR); Jin Wook Jang, Seoul (KR); Kwang Sung Kim, Gyeonggi-do (KR); Won Il Yoo, Seoul (KR)

(73) Assignee: EYEGENE, INC., Seoul (KR)

( * ) Notice: Subject to any disclaimer, the term of this patent is extended or adjusted under 35 U.S.C. 154(b) by 38 days.

(21) Appl. No.: 13/995,188

(22) PCT Filed: Dec. 17, 2011

(86) PCT No.: PCT/KR2011/009759
§ 371 (c)(1),
(2), (4) Date: Jun. 18, 2013

(87) PCT Pub. No.: WO2012/081947
PCT Pub. Date: Jun. 21, 2012

(65) Prior Publication Data
US 2013/0273101 A1 Oct. 17, 2013

(30) Foreign Application Priority Data
Dec. 18, 2010 (KR) .................. 10-2010-0130357

(51) Int. Cl.
*A61K 39/39* (2006.01)
*A61K 39/145* (2006.01)
*A61K 39/29* (2006.01)
*A61K 39/04* (2006.01)
*A61K 39/07* (2006.01)
*A61K 39/095* (2006.01)
*A61K 39/21* (2006.01)
*A61K 39/245* (2006.01)
*A61K 39/25* (2006.01)
*A61K 39/102* (2006.01)
*A61K 39/00* (2006.01)

(52) U.S. Cl.
CPC .......... *A61K 39/39* (2013.01); *A61K 39/0018* (2013.01); *A61K 39/04* (2013.01); *A61K 39/07* (2013.01); *A61K 39/095* (2013.01); *A61K 39/102* (2013.01); *A61K 39/145* (2013.01); *A61K 39/21* (2013.01); *A61K 39/245* (2013.01); *A61K 39/25* (2013.01); *A61K 39/29* (2013.01); *A61K 39/292* (2013.01); *A61K 2039/55572* (2013.01); *C12N 2710/16634* (2013.01); *C12N 2710/16734* (2013.01); *C12N 2730/10134* (2013.01); *C12N 2740/16034* (2013.01); *C12N 2760/16134* (2013.01)

(58) Field of Classification Search
None
See application file for complete search history.

(56) References Cited

U.S. PATENT DOCUMENTS

| 6,207,157 | B1 | 3/2001 | Gu et al. | |
|---|---|---|---|---|
| 6,531,131 | B1 | 3/2003 | Gu et al. | |
| 2005/0042230 | A1* | 2/2005 | Anderson et al. | 424/186.1 |
| 2009/0220522 | A1 | 9/2009 | Cross et al. | |
| 2010/0112013 | A1* | 5/2010 | Lee et al. | 424/282.1 |

FOREIGN PATENT DOCUMENTS

| KR | 10-0740237 B1 | 7/2007 |
|---|---|---|
| WO | WO 0211760 A1 * | 2/2002 |

OTHER PUBLICATIONS

Kim et al. Meningococcal group A lipooligosaccharides (LOS): preliminary structural studies and characterization of serotype-associated and conserved LOS epitopes. Infect Immun. May 1994;62(5):1566-75.*
Garçon N. Preclinical development of AS04. Methods Mol Biol. 2010;626:15-27.*
Molecular Probes-Product Information. http://tools.lifetechnologies.com/content/sfs/manuals/mp23350.pdf. Dated Jan. 6, 2003.*
Jacquet et al. Immunogenicity of a recombinant varicella-zoster virus gE-IE63 fusion protein, a putative vaccine candidate against primary infection and zoster reactivation. Vaccine 20 (2002) 1593-1602.*
Kimura et al. Recombinant varicella-zoster virus glycoproteins E and I: immunologic responses and clearance of virus in a guinea pig model of chronic uveitis. J Infect Dis. Aug. 1998;178(2):310-7.*
Zostavax product information. http://www.merck.com/product/usa/pi_circulars/z/zostavax/zostavax_pi2.pdf.*
Varivax product information. https://www.merck.com/product/usa/pi_circulars/v/varivax/varivax_pi.pdf.*
Schenck et al. The Enhancement of Antibody Formation by *Escherichia coli* Lipopolysaccharide and Detoxified Derivatives. J Immunol 1969; 102:1411-1422.*
McIntire et al.Chemical, Physical, and Biological Properties of a Lipopolysaccharide from *Escherichia coli* K-235. Biochemistry, 1967, 6: 2363-2372.*
International Search Report for PCT/KR2011/009759.
A.F.M. Verheul et al. "Meningococca llipopolysaccharides: virulence factor and potential vaccine component" Microbiological Reviews, 1993, vol. 53, No. 1, pp. 34-49, ISSN 0146-0749. See abstract; p. 40, right col.—p. 41, left col.

* cited by examiner

*Primary Examiner* — Nick Zou
(74) *Attorney, Agent, or Firm* — Vorys, Sater, Seymour & Pease LLP; Mih Suhn Koh

(57) ABSTRACT

The present invention relates to a pharmaceutical vaccine composition comprising: (a) a pathogen-derived antigen selected from the group consisting of *Mycobacterium tuberculosis* antigen, *Bacillus anthracis* antigen, HAV (hepatitis A virus) antigen, HBV (hepatitis B virus) antigen, HCV (hepatitis C virus) antigen, HIV (human immunodeficiency virus) antigen, influenza virus antigen, HSV (herpes simplex virus) antigen, Hib (*Haemophilus influenzae* type b) antigen, *Neisseria meningitidis* antigen, *Corynebacterium diphtheriae* antigen, *Bordetella pertussis* antigen, *Clostridium tetani* antigen and Varicella virus antigen; (b) a deacylated non-toxic LOS (lipooligosaccharide); and (c) a pharmaceutically acceptable carrier.

7 Claims, 16 Drawing Sheets

VACCINE FOR INDUCING AN IMPROVED IMMUNE REACTION

CROSS REFERENCE TO RELATED APPLICATIONS AND CLAIM OF PRIORITY

This patent application is a National Phase application under 35 U.S.C. §371 of International Application No. PCT/KR2011/009759, filed Dec. 17, 2011, which claims priority to Korean Patent Application No. 10-2010-0130357 filed Dec. 18, 2010, entire contents of which are incorporated herein by reference.

FIELD OF THE INVENTION

The present invention relates to a vaccine for inducing an improved immune reaction.

DESCRIPTION OF THE RELATED ART

Recently, immunoadjuvants have been newly focused and utilized in various vaccines such as cervical cancer vaccines and influenza vaccines. Of them, bacterial DNA received attention as an anti-cancer agent since 1960's, and is successively researched up to now. However, bacterial DNA has not been used as an anti-cancer agent due to its low efficacy (Glick, J. L. The specificity of inhibition of tumor cell viability by DNA. *CancerRes.* 27:2338, 1967). In spite of this defect, it was demonstrated that bacterial DNA is known to activate various immune cells without serious side effects, and has many advantages as an adjuvant (McCluskie M J, et al., CpG DNA is a potent enhancer of systemic and mucosal immune responses against hepatitis B surface antigen with intranasal administration to mice. *J Immunol.* November 1;161(9):4463-6.1998).

For these effects of bacterial DNA, Yamamoto et al. in Japan argument that palindromic sequences containing CG play a crucial role in effects of bacterial DNA which are demonstrated by Krieg et al. (Yamamoto S. et al. Unique palindromic sequences in synthetic oligonucleotides are required to induce IFN and augment IFN-mediated natural killer activity. *J. Immunol.* 148:4072,1992 ; Krieg AM, Antitumor applications of stimulating toll-like receptor 9 with CpG oligodeoxynucleotides. *Curr. Oncol. Rep.* March; 6(2):88-95.2004). Based on CpG-related studies from the middle of 1990's, the concern for DNA anti-cancer agent leaded to deduce a probability of synthetic DNA (CpG-ODN) containing unmethylated CG as an anti-cancer agent, for example a study for S substitution in diester bonds to inhibit short synthetic DNA degradation. In this connection, CpG-ODN-related products were utilized in a clinical trial as an anti-cancer agent as well as an adjuvant.

However, there remains to be solved some problems including immunogenicity and still low anti-cancer activity of S substitution in diester bonds of CpG-ODN. On current clinic, CpG 7909 is a phosphothioate oligonucleotide which induces anti-DNA Ab (Clin Immunol. 2001 August;100(2): 157-63), and is closely associated with autoimmune disorders such as SLE (systemic lupus erythematosus) (J Clin Immunol. 1986 July;6(4):292-8). In addition, it has been known that phosphothioate structure functions as TI Ag, contributing to disturbance of immune protection against infections (Mol Immunol. 1998 December;35(18):1161-70).

In LPS known to have anti-cancer effect since 1950's, utilization of LPS was difficult because LPS in a range of ng results in death by sepsis. It is general opinion that the link between LPS and DNA causes serious cytotoxicity, and thus the elimination of LPS is understood as very important process in DNA-related medicaments (Gao J J. et. al, Bacterial DNA and lipopolysaccharide induce synergistic production of TNF-alpha through a post-transcriptional mechanism. *J Immunol* 166(11):6855-60, 2001). In respect with efficacies, it should be considered that immune responses stimulated by LPS are much stronger than those by DNA whereas are Th2-type responses, not Th1-type which is important to anti-cancer, supposing LPS is not suitable as an anti-cancer agent (Lebman D A et al Interleukin 4 causes isotype switching to IgE in T cell-stimulated clonal B cell cultures. *J Exp Med*. September 1;168(3):853-62. 1988). Given that Th2-type immune activity inhibits Th1-type immune activity, it was very difficult to utilize LPS as an anti-cancer agent due to Th2-type immune activity stimulated by LPS (Rengarajan J et al. Transcriptional regulation of Th1/Th2 polarization. Immunol Today. October;21(10):479-83. 2000).

A variety of attempts to LPS detoxification have been studied, leading to successfully reduce its cytotoxicity through removal of polysaccharide chain or deacylation of lipid A (Katz SS et al Deacylation of lipopolysaccharide in whole *Escherichia coli* during destruction by cellular and extracellular components of a rabbit peritoneal inflammatory exudate. J Biol Chem. December 17;274(51):36579-84 1999). For example, monophosphoryl lipid A (MPL) is obtained by phosphorylation of lipid A in which polysaccharide chain of LPS is eliminated to develop an immunotherapeutic anti-cancer agent. However, its efficacy is known to be quite low.

On the other hand, the present applicants have already developed a novel immunoadjuvant to complement drawbacks of the above-mentioned immunoadjuvants (Korean Patent No. 0740237 (2007 Jul. 10)).

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY

The present inventors have made intensive studies to develop a novel vaccine composition which may overcome problems of conventional vaccines, and increase the efficacy of vaccines. As results, they have discovered that a non-toxic LOS (lipooligosaccharide) may be used as an immunoadjuvant in immunization using antigens of various pathogens, whereby immune responses are induced much more notable than those by conventional vaccines, enabling to function as an excellent vaccine for preventing various diseases.

Accordingly, it is an object of this invention to provide a pharmaceutical vaccine composition.

It is another object of this invention to provide a composition for inducing maturation of dendritic cells.

Other objects and advantages of the present invention will become apparent from the detailed description to follow taken in conjugation with the appended claims and drawings.

Technical Solutions of this Invention

In one aspect of the present invention, there is provided a pharmaceutical vaccine composition including:

(a) a pathogen-derived antigen selected from a group consisting of *Mycobacterium tuberculosis* antigen, *Bacillus*

*anthracis* antigen, HAV (Hepatitis A virus) antigen, HBV (Hepatitis B virus) antigen, HCV (Hepatitis C virus) antigen, HIV (human immunodeficiency virus) antigen, influenza virus antigen, HSV (Herpes simplex virus) antigen, Hib (*Haemophilus influenzae* type b) antigen, *Neisseria meningitidis* antigen, *Corynebacterium diphtheria* antigen, *Bordetella pertussis* antigen, *Clostridium tetani* antigen and Varicella virus antigen;

(b) a deacylated non-toxic LOS (Lipooligosaccharide); and (c) a pharmaceutically acceptable carrier.

The present inventors have made intensive studies to develop a novel vaccine composition which may overcome problems of conventional vaccines, and increase the efficacy of vaccines. As results, they have discovered that a non-toxic LOS (lipooligosaccharide) may be used as an immunoadjuvant in immunization using antigens of various pathogens, whereby immune responses are induced much more notable than those by conventional vaccines, enabling to function as an excellent vaccine for preventing various diseases.

The present invention is useful in vaccine to *Mycobacterium tuberculosis* causing tuberculosis.

*Mycobacterium tuberculosis* antigen used in the present invention includes various *Mycobacterium tuberculosis*—derived antigens conventionally known. Preferably, a suitable *Mycobacterium tuberculosis* antigen for the present invention is at least one antigen selected from a group consisting of 65 kD heat shock protein (HSP65), antigen 85A (Ag85A), antigen 85B, antigen 85C, ESAT-6, Des protein, MPT32, MPT51, MPT63, MPT64, HspX and Phosphate binding protein 1.

More preferably, *Mycobacterium tuberculosis* antigen used in the present *Mycobacterium tuberculosis* vaccine is at least one antigen selected from a group consisting of antigen 85A (Ag85A), ESAT-6, HspX and Phosphate binding protein 1.

In addition, the present invention is useful in vaccine to *Bacillus anthracis* causing anthrax.

*Bacillus anthracis* antigen used in the present invention includes various *Bacillus anthracis*—derived antigens conventionally known. Preferably, a suitable *Bacillus anthracis* antigen for the present invention is PA (protective antigen), LF (lethal antigen) or EA (edema antigen), and more preferably PA (protective antigen).

In addition, the present invention is useful in vaccine to HAV (Hepatitis A virus) causing Hepatitis A. HAV antigen used in the present invention includes various HAV—derived antigens conventionally known. Preferably, a suitable HAV antigen for the present invention is selected from a group consisting of live attenuated HAV, inactivated attenuated HAV, VP1, VP2, VP3, VP4, 2A, 2B, 2C, 3A, 3B, 3C and 3D protein, and more preferably inactivated attenuated HAV.

The present invention is useful in vaccine to HBV (Hepatitis B virus) causing

Hepatitis B. HBV antigen used in the present invention includes various HBV—derived antigens conventionally known. Preferably, a suitable HBV antigen for the present invention is HBcAg (core antigen of HBV) or HBsAg (surface antigen of HBV), and more preferably HBsAg.

The present invention is useful in vaccine to HCV (Hepatitis C virus) causing

Hepatitis C. HCV antigen used in the present invention includes various HCV—derived antigens conventionally known. Preferably, a suitable HCV antigen for the present invention is E1, E2 or NS3/4a antigen, and more preferably NS3.

The present invention is useful in vaccine to HIV causing AIDS. HIV antigen used in the present invention includes various HIV—derived antigens conventionally known. Preferably, a suitable HIV antigen for the present invention is Gag (p55gag), Pol, Vif, Vpr, Tat, Rev, Vpu, Env or Nef antigen, and more preferably Env antigen.

The present invention is useful in vaccine to influenza causing influenza. Influenza antigen used in the present invention includes various influenza—derived antigens conventionally known. Preferably, a suitable influenza antigen for the present invention is envelope glycoprotein HA or NA, and more preferably envelope glycoprotein HA.

The present invention is useful in vaccine to HSV (Herpes simplex virus) causing herpes simplex. HSV antigen used in the present invention includes various HSV—derived antigens conventionally known. Preferably, a suitable HSV antigen for the present invention is glycoprotein gB, gD or gH, and more preferably glycoprotein gB or gD.

The present invention is useful in vaccine to Hib (*Haemophilus influenzae* type b) causing meningitis. Hib antigen used in the present invention includes various Hib—derived antigens conventionally known. Preferably, a suitable Hib antigen for the present invention is glycoprotein PRP [*Haemophilus* type b capsular polysaccharide (polyribosyl-ribitol-phosphate)] or its conjugate, and more preferably conjugate of PRP and tetanus toxin.

The present invention is useful in vaccine to *Neisseria meningitidis* causing encephalomeningitis. *Neisseria meningitidis* antigen used in the present invention includes various *Neisseria meningitidis*—derived antigens conventionally known. Preferably, a suitable *Neisseria meningitidis* antigen for the present invention is PI, PII, PIII, pilin, lipopolysaccharide, iron binding protein or proteosome, and more preferably proteosome.

The present invention is useful in vaccine to *Corynebacterium diphtheria* causing diphtheria. *Corynebacterium diphtheria* antigen used in the present invention includes various *Corynebacterium diphtheria*—derived antigens conventionally known. Preferably, a suitable *Corynebacterium diphtheria* antigen for the present invention is Diphtheria toxin.

The present invention is useful in vaccine to *Bordetella pertussis* causing pertussis. *Bordetella pertussis* antigen used in the present invention includes various *Bordetella pertussis*—derived antigens conventionally known. Preferably, a suitable *Bordetella pertussis* antigen for the present invention is Pertusis toxin.

The present invention is useful in vaccine to *Clostridium tetani* causing pertussis. *Clostridium tetani* antigen used in the present invention includes various *Clostridium tetani*—derived antigens conventionally known. Preferably, a suitable *Clostridium tetani* antigen for the present invention is Tetanus toxin.

The present invention is useful in vaccine to Varicella virus causing pertussis. Varicella virus antigen used in the present invention includes various Varicella virus—derived antigens conventionally known. Preferably, a suitable Varicella virus antigen for the present invention is live attenuated Varicella virus, inactivated attenuated Varicella virus, gpI or gpII, and more preferably live attenuated Varicella virus.

It is the most feature of the present pharmaceutical composition to utilize a deacylated non-toxic LOS (lipooligosaccharide) as an immunoadjuvant. The term "LOS (lipooligosaccharide)" adapted first herein refers to a modifier of LPS (lipopolysaccharide) with low molecular weight which has glycochains shorter than natural occurring LPS. LOS has a molecular weight in a range of 5,000-10,000 Da before deacylation. The term "deacylated LOS" used herein means a form of LOS that a fatty acid linked to glucosamine of lipid A via —C(O)O— bond is eliminated from LOS, resulting in significant reduction of cytotoxicity compared to LOS. The fatty acid is linked to glucosamine of lipid A through —C(O)O— bond and —C(O)NH— bond. The deacylated LOS of the present invention is a LOS of which the fatty acid linked by —C(O)O— bond is removed by deacylation of lipid A.

The deacylated non-toxic LOS of the present invention may be prepared according to various methods, for example methods disclosed in previous patents of the present inventors including Korean Patent No. 0456681; WO 2004/039413; Korean Patent No. 0740237; and WO 2006/121232. For instance, a portion of fatty acid in LOS is removed and detoxificated from lipid A through deacylation via strong base treatment (e.g., 2 N NaOH) to LPS (lipopolysaccharide).

According to a preferable embodiment, the deacylated non-toxic LOS used as an immunoadjuvant in the present invention is detoxificated by deacylation of lipid A via alkaline treatment to LPS (lipopolysaccharide). Preferred example of the alkaline treatment includes NaOH, KOH, $Ba(OH)_2$, CsOH, $Sr(OH)_2$, $Ca(OH)_2$, LiOH, RbOH and $Mg(OH)_2$, more preferably NaOH, KOH, $Ba(OH)_2$, $Ca(OH)_2$, LiOH and $Mg(OH)_2$, much more preferably NaOH, KOH and $Mg(OH)_2$, and most preferably NaOH.

The detoxification extent of LPS may be analyzed according to various methods known to those ordinarily skilled in the art. For example, the detoxification may be determined by measuring an amount of TNF-$\alpha$ (tumor necrosis factor-$\alpha$) secreted in THP-1 (acute monocytic leukemia) treated with LPS. The deacylated non-toxic LOS of the present invention induces a relatively little amount of TNF-$\alpha$ secretion compared with conventional LPS.

It is another feature that the deacylated non-toxic LOS of the present invention has lower molecular weight than conventional LPS to be used in general. Preferably, the deacylated non-toxic LOS used in the present invention has a molecular weight in a range of 1,500-10,000 Da, more preferably 2,000-5,000 Da, much more preferably 2,000-4,000 Da, still much more preferably 3,000-4,000 Da, and most preferably 3,200-3,700 Da. Measurement of molecular weight may be carried out using a conventional method, for example MALDI-MASS.

According to a preferable embodiment, the deacylated non-toxic LOS of this invention is derived from *Escherichia coli* (*E. coli*), and most preferably *E. coli* EG0021 (KCCM 10374) isolated by the present inventors.

The deacylated non-toxic LOS used in the present invention is very suitable for the vaccine composition of this invention due to much excellent immunostimulatory effect and significantly low cytotoxicity compared with conventional immunoadjuvants. As demonstrated in Examples below, the deacylated non-toxic LOS of this invention has much lower cytotoxicity than monophosphoryl lipid A (MPL) obtained through phosphorylation of lipid A from which a polysaccharide chain of LPS is removed to reduce LPS cytotoxicity.

As shown in Example below, the administration of the deacylated non-toxic LOS of the present invention with antigens of various pathogens also induces the level of immune response, demonstrating that the deacylated non-toxic LOS of the present invention may synergistically induce immune responses together with antigens of various pathogens.

The vaccine composition of the present invention may contribute to a preventive efficacy on a certain disease only in a fundamental composition containing antigen of pathogen and deacylated non-toxic LOS. Alternatively, the vaccine composition of the present invention may further include other immunoadjuvant, for example including a Group II element selected from the group consisting of Mg, Ca, Sr, Ba and Ra; a Group IV element selected from the group consisting of Ti, Zr, Hf and Rf; or an aluminium salt or a hydrate thereof Preferably, the salt is formed with oxide, peroxide, hydroxide, carbonate, phosphate, pyrophosphate, hydrogen phosphate, dihydrogen phosphate, sulfate or silicate. For example, the immunoadjuvant capable of being additionally used in the vaccine composition of the present invention includes magnesium hydroxide, magnesium carbonate hydroxide, pentahydroxide, titanium dioxide, calcium carbonate, barium oxide, barium hydroxide, barium peroxide, barium sulfate, calcium sulfate, calcium pyrophosphate, magnesium carbonate, magnesium oxide, aluminum hydroxide, aluminum phosphate and hydrated aluminum potassium sulfate (Alum). Most preferably, the immunoadjuvant capable of being additionally used in the vaccine composition of the present invention is aluminum hydroxide.

In the pharmaceutical vaccine compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered via the oral or parenterally. When the pharmaceutical composition of the present invention is administered parenterally, it can be done by intravenous, subcutaneous, intramuscular, abdominal and transdermal administration.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Preferably, the pharmaceutical composition of the present invention is administered with a daily dose of 0.0001-1,000 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further include dispersant or stabilizer.

The pharmaceutical vaccine composition of the present invention induces strong immune responses against pathogen, and thus has excellent potency for preventing a certain disease. In addition, the pharmaceutical vaccine composition of the present invention possesses superior stability because the deacylated non-toxic LOS used as an immuno-adjuvant in the present invention has almost no cytotoxicity.

Among various antigens of pathogens, the deacylated non-toxic LOS used in the present invention has a very excellent immunostimulatory effect in immune response against *Mycobacterium tuberculosis* antigen, *Bacillus anthracis* antigen, HAV (Hepatitis A virus) antigen, HBV (Hepatitis B virus) antigen, HCV (Hepatitis C virus) antigen, HIV (human immunodeficiency virus) antigen, influenza virus antigen, HSV (Herpes simplex virus) antigen, Hib (*Haemophilus influenzae* type b) antigen, *Neisseria meningitidis* antigen, *Corynebacterium diphtheria* antigen, *Bordetella pertussis* antigen, *Clostridium tetani* antigen and Varicella virus antigen, as demonstrated in Examples below.

In another aspect of the present invention, there is provided a composition for inducing maturation of dendritic cells, including a deacylated non-toxic LOS (Lipooligosaccharide).

In still another aspect of the present invention, there is provided a method for preparing maturated dendritic cells, including incubating immature dendritic cells with a deacylated non-toxic LOS (Lipooligosaccharide).

In the preparation of dendritic cell vaccine, dendritic cells isolated from in vivo have to mature. In this process, the deacylated non-toxic LOS (Lipooligosaccharide) may be very useful.

According to the method for preparing dendritic cell vaccine, immature dendritic cells are derived from monocytes or hematopoietic stem cells, and more preferably monocytes, because dendritic cells with uniform properties from monocytes may be obtained in a faster manner than pluripotent hematopoietic stem/progenitor cells.

According to a preferred embodiment, monocytes are collected from peripheral blood. The method for obtaining immature dendritic cells from progenitor cells (e.g., monocytes or hematopoietic stem cells) in peripheral blood may be conducted with the form of the progenitor cells isolated or unisolated from other cells in peripheral blood.

Afterward, monocytes obtained from peripheral blood are induced to differentiate to dendritic cells. Monocytes are cultured in media containing suitable cytokines for the differentiation to dendritic cells. The cytokines are GM-CSF (Granulocyte macrophage colony stimulating factor), IL-4 (interleukin-4), IL-13 or the combination thereof An appropriate amount of cytokines added is a sufficient amount to differentiate dendritic cells, and it may be selected empirically by researchers in the laboratory.

Where cytokines are used in first incubation for differentiating dendritic cells from monocytes, the incubation time is commonly more than 5 days, and preferably 6-7 days.

Finally, maturation process is conducted using immature dendritic cells obtained from the differentiation process described above. i.e., Dendritic cells are matured by culturing in incubator with media containing the present deacylated non-toxic LOS. Secondary incubation time is commonly more than 10 hrs, and preferably more than 20 hrs, e.g. 1-3 days.

The present invention may prepare effectively matured dendritic cells vaccine.

The features and advantages of this invention will be summarized as follows:

(a) The present vaccine composition uses pathogen-derived antigen and a deacylated non-toxic LOS as immunoadjuvant.

(b) A deacylated non-toxic LOS as immunoadjuvant has a very excellent immunostimulatory effect in immune response against certain pathogen, and possesses superior stability because it has almost no cytotoxicity.

(c) In addition, a deacylated non-toxic LOS enables to prepare effectively maturated dendritic cells vaccine.

BRIEF DESCRIPTION OF THE DRAWINGS

In FIGS. 2a-d, Ag85A, HspX, Phosphate binding protein 1, and ESAT-6 were used as antigen to *Mycobacterium tuberculosis*, respectively.

In FIGS. 9a-b, gD antigen and gB antigen were used as antigen, respectively.

In FIGS. 12a-c, Diphtheria toxin, Pertusis toxin and Tetanus toxin were used as antigen, respectively.

BEST MODE FOR CARRYING OUT THE INVENTION DETAILED DESCRIPTION

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Manufacturing a Very Short Lipooligosaccharide (LOS) CIA05 as a Novel Immunoadjuvant The inventors screened a strain (*E. coli* EG0021) having a very short sugar chain of lipopolysaccharide from *Escherichia coli* living in the bowls of healthy humans and deposited the strain *E. coli* EG0021 to the Korean Culture Center of Microorganisms (KCCM) on May 2, 2002, its accession number KCCM 10374 (c.f., Republic of Korea Pat. No. 0456681; WO 2004/039413; Korean Pat. No. 0740237; WO 2006/121232). Purification of LPS from this strain was done according to the methods disclosed in Korean Pat. No. 0456681; WO 2004/039413; Korean Pat. No. 0740237; and WO 2006/121232. The molecular weight of the LPS was 3,500 Da estimated by MALDI-MASS (Shimadz, Axima-LNR V 2.3.5 (Mode Liner, Power: 106)). The toxicity of the purified LPS was removed by following the protocols disclosed in Korean Pat. No. 0456681; WO 2004/039413; Korean Pat. No. 0740237; and WO 2006/121232. The purified *E. coil* lipopolysaccharide was adjusted to a concentration of 3 mg/ml, and 2 N NaOH was mixed with the lipopolysaccharide at a mixing ratio of 1:1 (by volume), deacylated for 140 minutes while shaking at 60° C. every 10 minute. 1 N acetic acid at a volume about ⅕ of the initial 0.2 N NaOH were added to titrate the pH to 7.0. After titration, the resulting mixture was precipitated by ethanol to obtain non-toxic lipooligosaccharide (CIA05).

Example 2

Comparing the Toxicity of the Novel Adjuvant CIA05 with Conventional Adjuvant MPL The novel adjuvant CIA05 developed in this invention to be used for a vaccine was compared with the conventional MPL (Monophosphoryl lipid A) for its toxicity. Human PBMCs (Peripheral Blood Mononuclear Cell) from healthy human donors were seeded at $5\times10^5$ cell/ml in a 24-well tissue culture plate. 1 ml of the growth medium (RPMI 1640(Gibco)+10% FBS(Gibco)) was added to each well. The mixture was treated with conditions as follows: 1) negative control BSS (Balanced salt solution) 100 µl; 2) deacylated non-toxic LOS (CIA05) 10 µg/100 µl; and 3) MPL (*E. coli* F583 MPL) 10 µg/100 µl.

Figure 1:
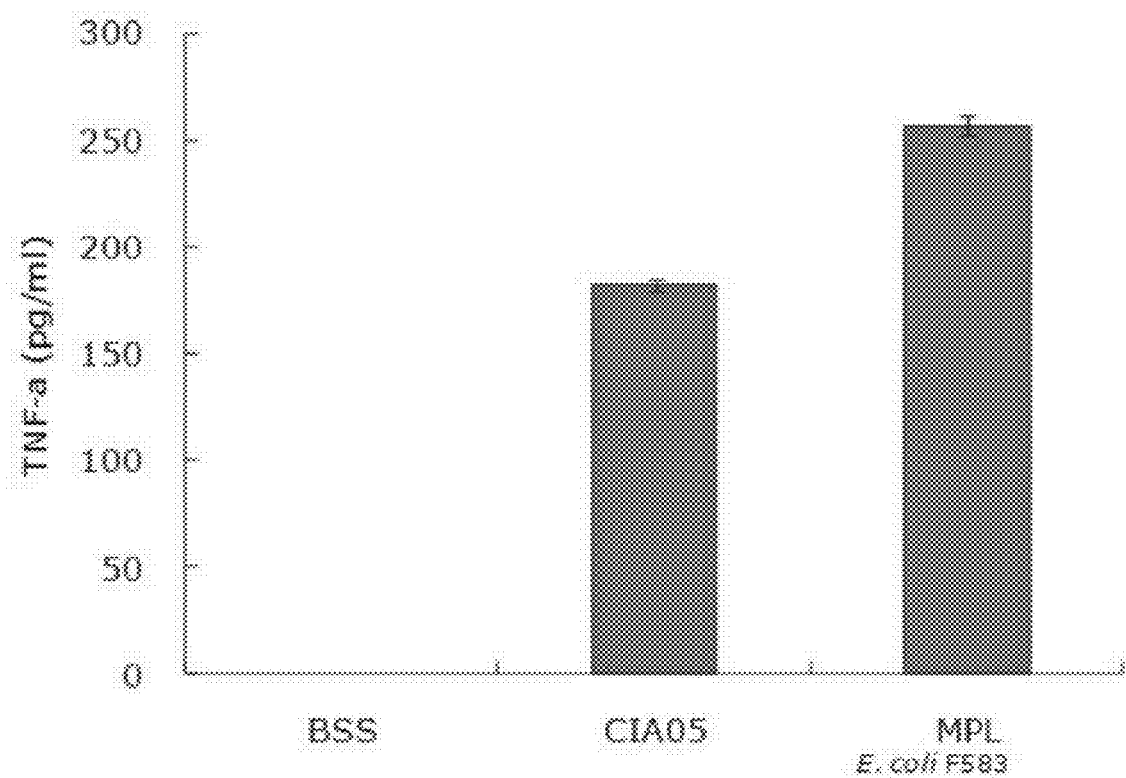
FIG. 1 is a graph showing that the novel adjuvant CIA05 has less cytotoxicity than MPL (TNF-αsecretion).

After 12 hrs, the treated medium were pooled and centrifuged. The level of TNF-α secreted by THP-1 (Acute monocytic leukemia) was quantified using ELISA kit (R&D system, DY210). As shown in FIG. 1, CIA05 showed ⅓ lesser toxicity compared to the conventional adjuvant MPL.

Example 3

Efficacy Analysis on the Present Vaccine to *Mycobacterium Tuberculosis*

Immunization of *Mycobacterium Tuberculosis* Vaccine Antigen and Adjuvant CIA05
a. In order to verify efficacy of adjuvant CIA05 for *Mycobacterium tuberculosis* vaccine, 4 antigens of *Mycobacterium tuberculosis* were used. They were Ag85A (32-kDa), HspX (16-kDa), Phosphate binding protein 1 (38-kDa) and ESAT-6 (6-kDa). Six-week old Balb/c mice (SLC, Japan) were injected for 3-times at 1-week interval with the antigens (each 2 µg) alone or the mixture including Alum (aluminum hydroxide; Brenntag, Germany) or CIA05 in the final volume of 100 µl.

Titer Measurement of *Mycobacterium Tuberculosis* Vaccine Antigen-Specific Antibody In order to measure titer of *Mycobacterium tuberculosis* antigen-specific antibody in serum after immunization, endpoint ELISA method (Enzyme-Linked Immunosorbent Assay) to was used. 96-well plate was coated with 100 µl of Ag85A (32-kDa), HspX (16-kDa), Phosphate binding protein 1 (38-kDa) and ESAT-6 (6-kDa) with concentration of 1 µg/ml, respectively. Then, the plate was blocked with 300 µl of 1% BSA (Bovine Serum Albumin) for 1 hr at room temperature. After blocking, each well was washed three times with PBS containing 0.05% Tween-20 and incubated with 100 µl of serum which is obtained after immunization for 2 hrs at 37° C. In order to determine *Mycobacterium tuberculosis* antigen-specific antibody, the plate was reacted with horse radish peroxidase-conjugated anti-mouse IgG (Zymed), subsequently added with TMB (tetramethylbenzidine, BD Bio Science, 55555214) and stopped with 1 N $H_2SO_4$. The level of *Mycobacterium tuberculosis* antigen-specific antibody in serum after immunization was verified by measuring absorbance at 450 nm.

Efficacy Analysis of Adjuvant CIA05 on *Mycobacterium Tuberculosis* Vaccine

Figure 2A:
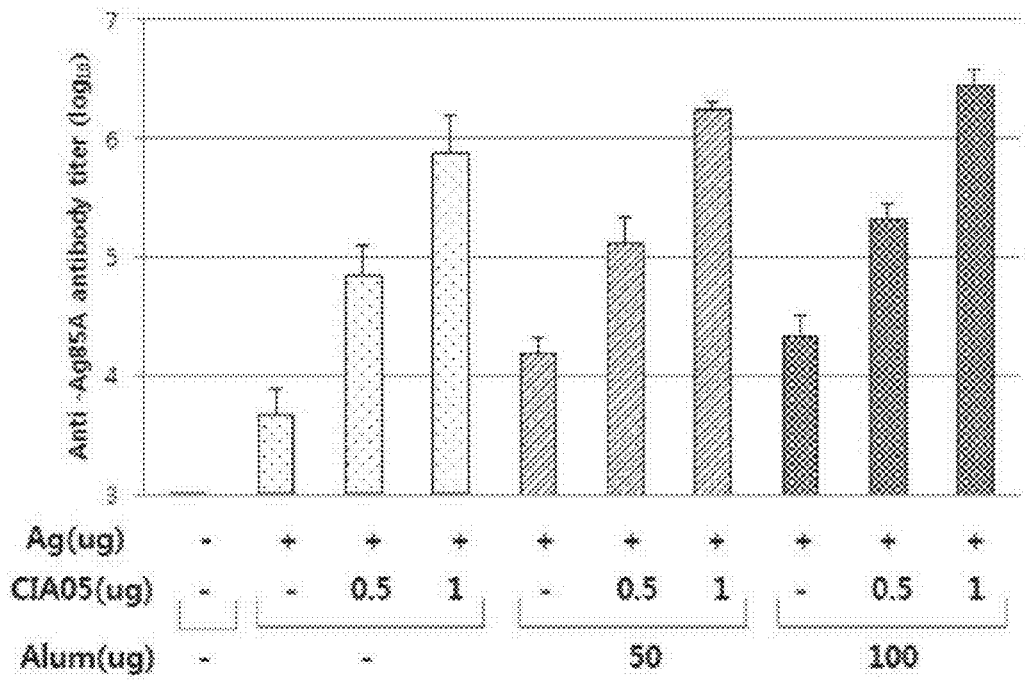
FIGS. 2a-d are results of efficacy analysis on the present vaccine to *Mycobacterium tuberculosis*.

As a result of analyzing efficacies for 4 antigens of *Mycobacterium tuberculosis* and adjuvant CIA05, in case of Ag85A (32-kDa), the production of *Mycobacterium tuberculosis* antigen-specific antibody in the Alum group was increased by approximately 4 times (50 µg of Alum) or approximately 8 times (100 µg of Alum) as compared to the antigen alone group. Moreover, the production of *Mycobacterium tuberculosis* antigen-specific antibody in the CIA05 group was increased by approximately 16 times (0.5 µg of CIA05) or approximately 128 times (1.0 µg of CIA05) as compared to the antigen alone group (FIG. 2*a*). In addition, where CIA05 was used, the production level of *Mycobacterium tuberculosis* antigen-specific antibody was remarkably increased in a dose-dependent manner, indicating that CIA05 is a very suitable adjuvant for *Mycobacterium tuberculosis* antigen Ag85A. Meanwhile, where the adjuvant CIA05 and Alum were used together, the production level of *Mycobacterium tuberculosis* antigen-specific antibody was increased by approximately 2 times (50 µg of Alum) or approximately 4 times (100 µg of Alum) as compared to the 0.5 µg of CIA05 alone group. Where the adjuvant CIA05 and Alum were used together, the production level of *Mycobacterium tuberculosis* antigen-specific antibody was increased by approximately 2 times (50 µg of Alum) or approximately 4 times (100 µg of Alum) as compared to the 1.0 µg of CIA05 alone group.

Figure 2B:
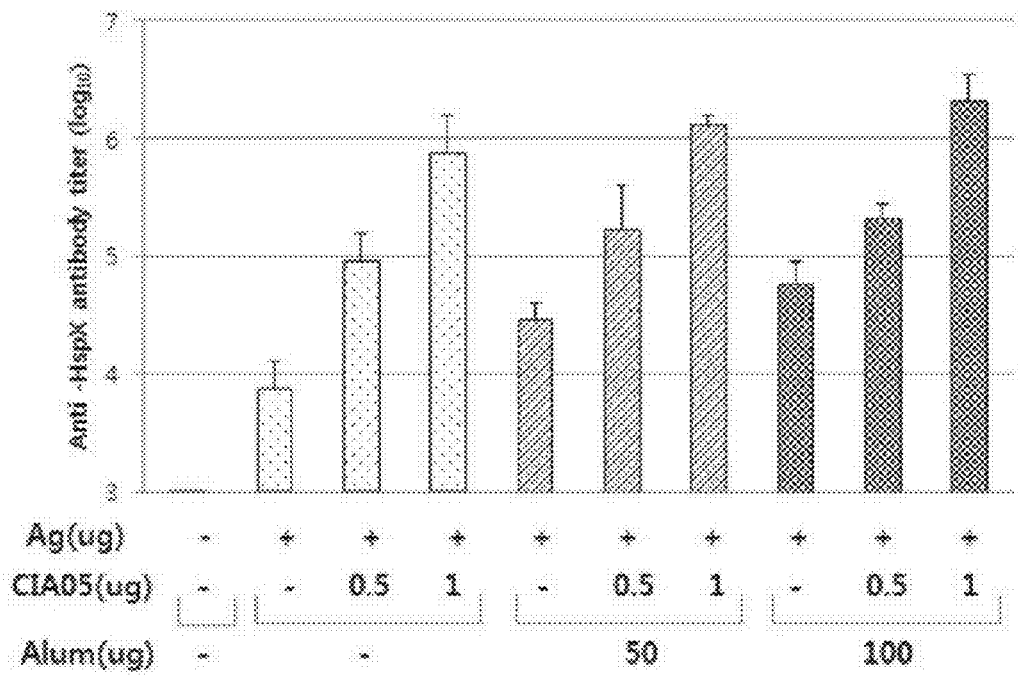

In case of HspX (16-kDa), the production of *Mycobacterium tuberculosis* antigen-specific antibody in the Alum group was increased by approximately 4 times (50 µg of Alum) or approximately 8 times (100 µg of Alum) as compared to the antigen alone group. Moreover, the production of *Mycobacterium tuberculosis* antigen-specific antibody in the CIA05 group was increased by approximately 16 times (0.5 µg of CIA05) or approximately 128 times (1.0 µg of CIA05) as compared to the antigen alone group (FIG. 2*b*). In addition, where CIA05 was used, the production level of *Mycobacterium tuberculosis* antigen-specific antibody was remarkably increased in a dose-dependent manner, indicating that CIA05 is a very suitable adjuvant for *Mycobacterium tuberculosis* antigen HspX (16-kDa). Meanwhile, where the adjuvant CIA05 and Alum were used together, the production level of *Mycobacterium tuberculosis* antigen-specific antibody was increased by approximately 2 times (50 µg of Alum) or approximately 4 times (100 µg of Alum) as compared to the 0.5 µg of CIA05 alone group. Where the adjuvant CIA05 and Alum were used together, the production level of *Mycobacterium tuberculosis* antigen-specific antibody was increased by approximately 2 times (50 µg of Alum) or approximately 4 times (100 µg of Alum) as compared to the 1.0 µg of CIA05 alone group.

Figure 2C:
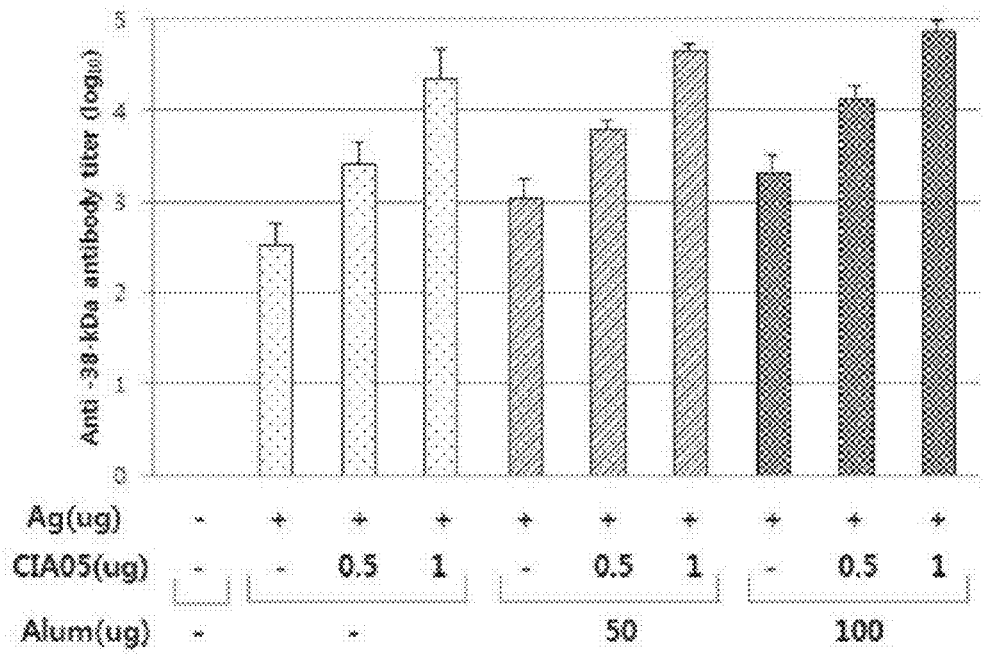

In case of Phosphate binding protein 1 (38-kDa), the production of *Mycobacterium tuberculosis* antigen-specific antibody in the Alum group was increased by approximately 4 times (50 µg of Alum) or approximately 8 times (100 µg of Alum) as compared to the antigen alone group. Moreover, the production of *Mycobacterium tuberculosis* antigen-specific antibody in the CIA05 group was increased by approximately 8 times (0.5 µg of CIA05) or approximately 64 times (1.0 µg of CIA05) as compared to the antigen alone group (FIG. 2c). In addition, where CIA05 was used, the production level of *Mycobacterium tuberculosis* antigen-specific antibody was remarkably increased in a dose-dependent manner, indicating that CIA05 is a very suitable adjuvant for *Mycobacterium tuberculosis* antigen Phosphate binding protein 1 (38-kDa). Meanwhile, where the adjuvant CIA05 and Alum were used together, the production level of *Mycobacterium tuberculosis* antigen-specific antibody was increased by approximately 2 times (50 µg of Alum) or approximately 4 times (100 µg of Alum) as compared to the 0.5 µg of CIA05 alone group. Where the adjuvant CIA05 and Alum were used together, the production level of *Mycobacterium tuberculosis* antigen-specific antibody was increased by approximately 2 times (50 µg of Alum) or approximately 4 times (100 µg of Alum) as compared to the 1.0 µg of CIA05 alone group.

Figure 2D:
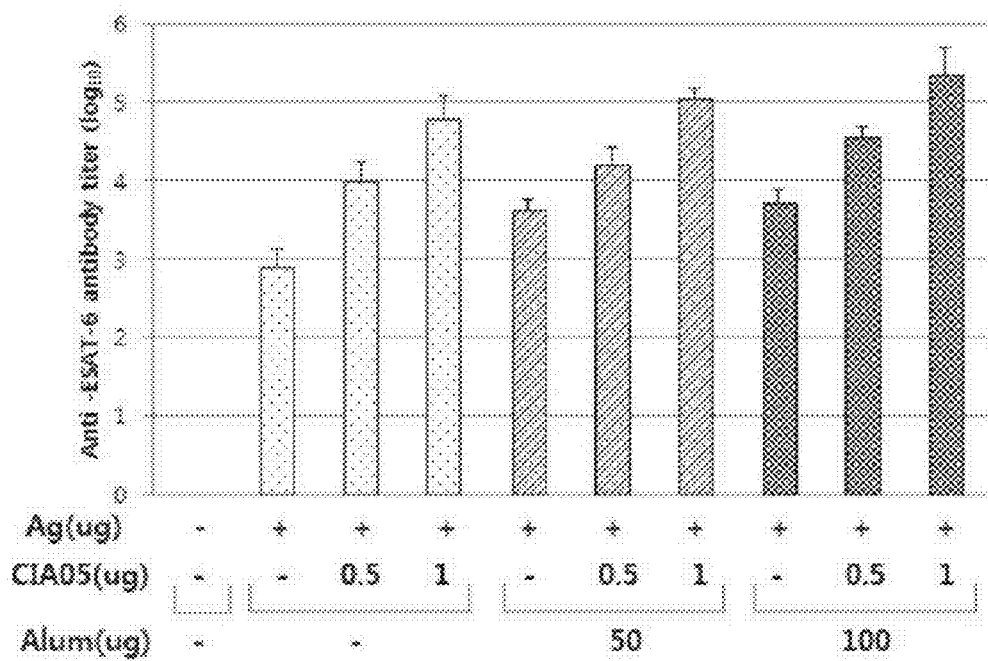

In case of ESAT-6 (6-kDa), the production of *Mycobacterium tuberculosis* antigen-specific antibody in the Alum group was increased by approximately 4 times (50 µg of Alum) or approximately 8 times (100 µg of Alum) as compared to the antigen alone group. Moreover, the production of *Mycobacterium tuberculosis* antigen-specific antibody in the CIA05 group was increased by approximately 16 times (0.5 µg of CIA05) or approximately 128 times (1.0 µg of CIA05) as compared to the antigen alone group (FIG. 2d). In addition, where CIA05 was used, the production level of *Mycobacterium tuberculosis* antigen-specific antibody was remarkably increased in a dose-dependent manner, indicating that CIA05 is a very suitable adjuvant for *Mycobacterium tuberculosis* antigen ESAT-6 (6-kDa). Meanwhile, where the adjuvant CIA05 and Alum were used together, the production level of *Mycobacterium tuberculosis* antigen-specific antibody was increased by approximately 2 times (50 µg of Alum) or approximately 4 times (100 µg of Alum) as compared to the 0.5 µg of CIA05 alone group. Where the adjuvant CIA05 and Alum were used together, the production level of *Mycobacterium tuberculosis* antigen-specific antibody was increased by approximately 2 times (50 µg of Alum) or approximately 4 times (100 µg of Alum) as compared to the 1.0 µg of CIA05 alone group.

Figure 2E:
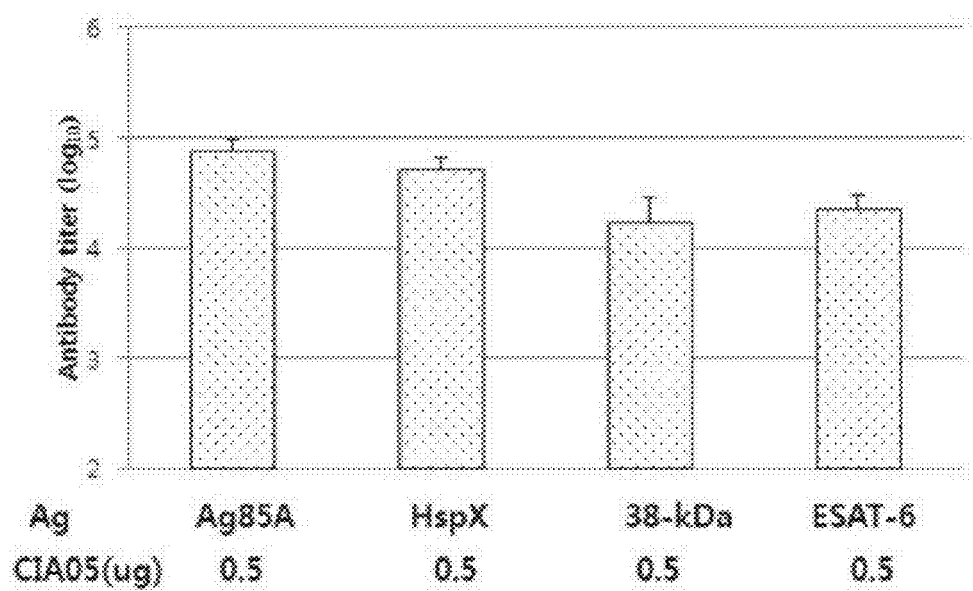
FIG. 2e is results of comparison on immunostimulatory effect of Ag85A, HspX, ESAT-6 and 38-kDa. CIA05 (0.5 μg) and antigens (each 2 μg) were used.

The test was conducted to select the best antigen for immunostimulatory effect among *Mycobacterium tuberculosis* antigens (FIG. 2e). As a result, the best antigen for immunostimulatory effect was Ag85A, HspX, ESAT-6 and 38-kDa in order. Therefore, it would be determined that the most appreciate antigen for the present CIA05 was Ag85A.

In conclusion, the present *Mycobacterium tuberculosis* vaccine including adjuvant CIA05 has the excellent immunization efficacy, i.e., vaccine efficacy and it has more excellent immunostimulatory effect to *Mycobacterium tuberculosis* antigen than that of the conventional adjuvant Alum.

Example 4

Efficacy Analysis on the Present Vaccine to *Bacillus Anthracis*

Immunization of *Bacillus Anthracis* Vaccine Antigen PA and Adjuvant CIA05

*Bacillus anthracis* is comprised of 3 proteins, PA (protective antigen), LF (lethal antigen) and EA (edema antigen). It produces 2 types of toxin. PA has been used for *Bacillus anthracis* vaccine. A recombinant full-length PA antigen was used in this experiment. Six-week old male Balb/c mice were intraperitoneally injected for 3-times at 2-week interval with the 10 µg of *Bacillus anthracis* PA antigen. 10 µg of PA antigen contained in the final volume of 100 µl was administered. 0.5 µg or 1.0 µg of CIA05 contained in the final volume of 100 µl was administered. 50 µg or 100 µg of Alum contained in the final volume of 100 µl was administered. The negative control was administered with PBS (Phosphate-Buffered Saline, pH 7.3) by 100 µl every time. After the third injection, whole blood were collected from mouse and centrifuged to obtain serum. In order to measure a specific antibody titer to PA antigen in serum after immunization, end-point ELISA method (Enzyme-Linked Immunosorbent Assay) was used as the same manner in Example 3.

Figure 3:
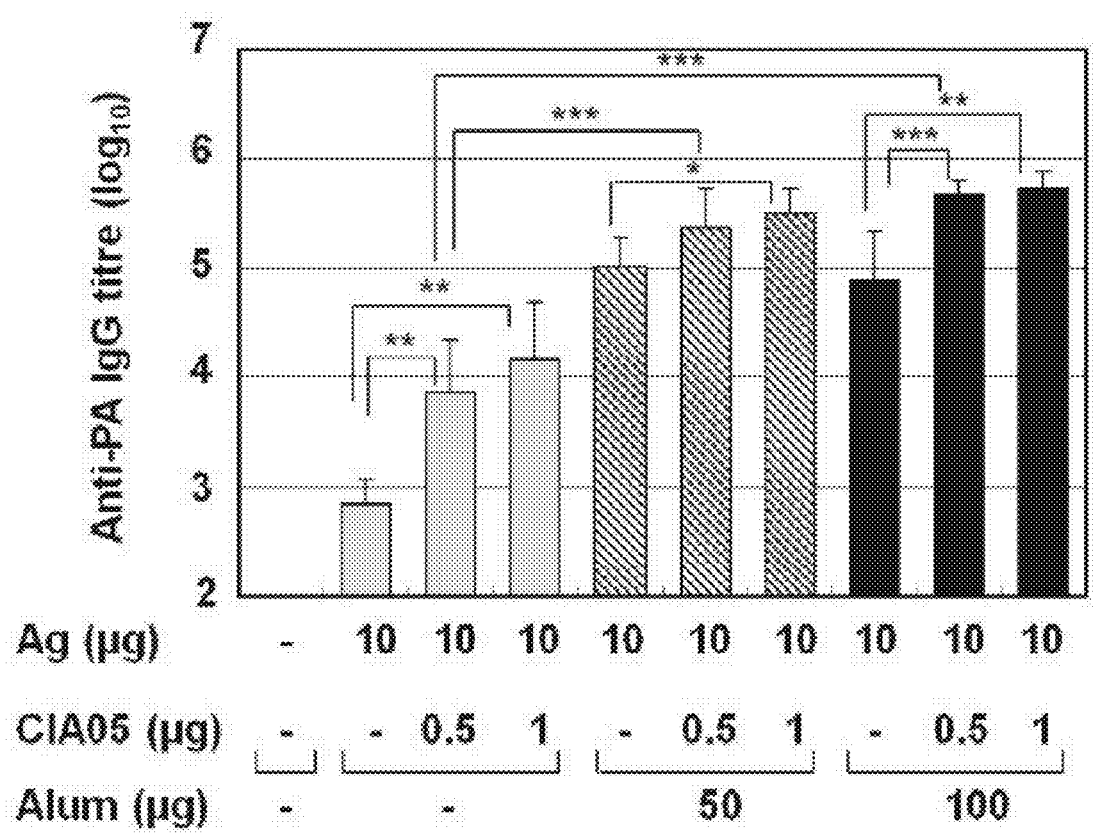
FIG. 3 is results of efficacy analysis on the present vaccine to *Bacillus anthracis*.

As a result of analyzing for PA-specific antigen in serum after immunization, where the adjuvant CIA05 was administered, PA-specific antigen was increased by approximately 10 times (0.5 µg of CIA05) and approximately 21 times (1.0 µg of CIA05) as compared to the PA antigen alone immunization, indicating that CIA05 play a role as the adjuvant with *Bacillus anthracis* antigen PA in *Bacillus anthracis* vaccine (FIG. 3). In addition, where the adjuvant CIA05 and Alum were used together, it could be determined CIA05 and Alum may improve PA-specific immunization (FIG. 3).

In conclusion, the present *Bacillus anthracis* vaccine including adjuvant CIA05, particularly, the *Bacillus anthracis* vaccine using the combination of PA antigen and CIA05has the excellent immunization efficacy, i.e., vaccine efficacy.

Example 5

Efficacy Analysis on the Present Vaccine to Hepatitis A Virus (HAV)

Inactivated HAV cultured in MRC-5 cell line was used as antigen. Six-week old male Balb/c mice were intraperitoneally injected for 3-times at 1-week interval with inactivated HAV alone or the mixture including CIA05. At 1 week after the third injection, whole blood were collected from mouse and centrifuged to obtain serum, and HAV-specific antibody titer was measured with end-point ELISA method (Enzyme-Linked Immunosorbent Assay) as the same manner in Example 3.

Figure 4:
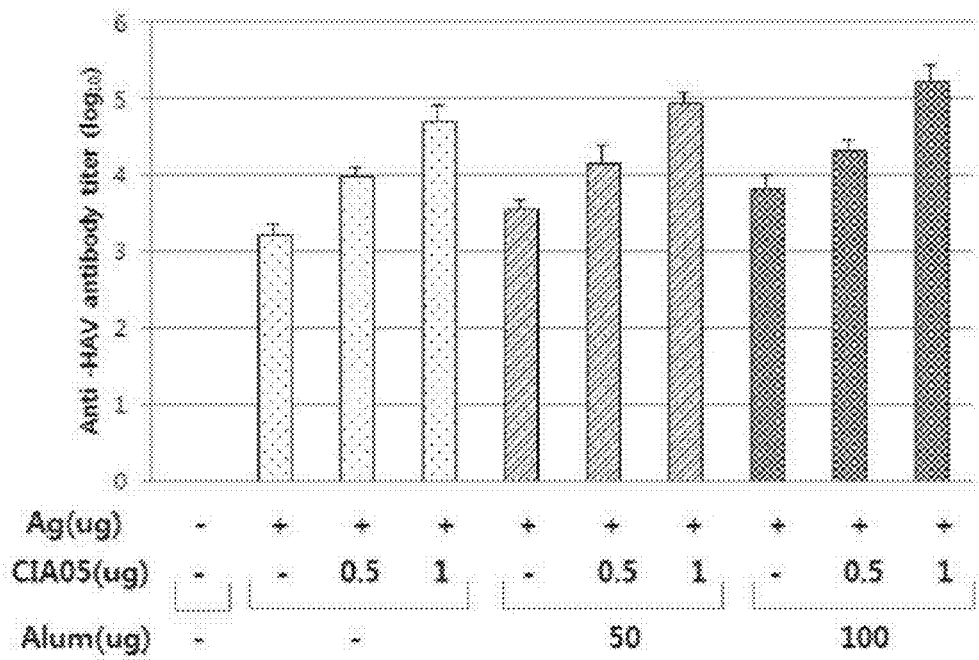
FIG. 4 is results of efficacy analysis on the present vaccine to HAV (Hepatitis A virus).

As a result, the production of HAV antigen-specific antibody in the Alum group was increased by approximately 2 times (50 μg of Alum) or approximately 4 times (100 μg of Alum) as compared to the antigen alone group. Moreover, the production of HAV antigen-specific antibody in the CIA05 group was increased by approximately 8 times (0.5 μg of CIA05) or approximately 32 times (1.0 μg of CIA05) as compared to the antigen alone group (FIG. 4). In addition, where CIA05 was used, the production level of HAV antigen-specific antibody was remarkably increased in a dose-dependent manner, indicating that CIA05 is a very suitable adjuvant for HAV antigen (inactivated HAV). Meanwhile, where the adjuvant CIA05 and Alum were used together, the production level of HAV antigen-specific antibody was increased by approximately 2 times (50 μg of Alum) or approximately 4 times (100 μg of Alum) as compared to the 0.5 μg of CIA05 alone group. Where the adjuvant CIA05 and Alum were used together, the production level of HAV antigen-specific antibody was increased by approximately 2 times (50 μg of Alum) or approximately 4 times (100 μg of Alum) as compared to the 1.0 μg of CIA05 alone group.

In conclusion, the present HAV vaccine including adjuvant CIA05, particularly, the HAV vaccine using the combination of inactivated HAV and CIA05 has the excellent immunization efficacy, i.e., vaccine efficacy.

Example 6

Efficacy Analysis on the Present Vaccine to Hepatitis B Virus (HBV)

HBV surface antigen HBsAg (adr subtype) was expressed in *Hansenula polymorpha* to obtain recombinant HBsAg. The recombinant HBsAg was purified and used as an antigen to HBV vaccine. Balb/c mice were injected for 3-times at 1-week interval with 2 μg of HBV antigen HBsAg alone or the mixture including Alum or CIA05. At 1 week after the third injection, whole blood were collected from mouse and centrifuged to obtain serum, and HBsAg-specific antibody titer was measured with end-point ELISA method (Enzyme-Linked Immunosorbent Assay) as the same manner in Example 3.

Figure 5:
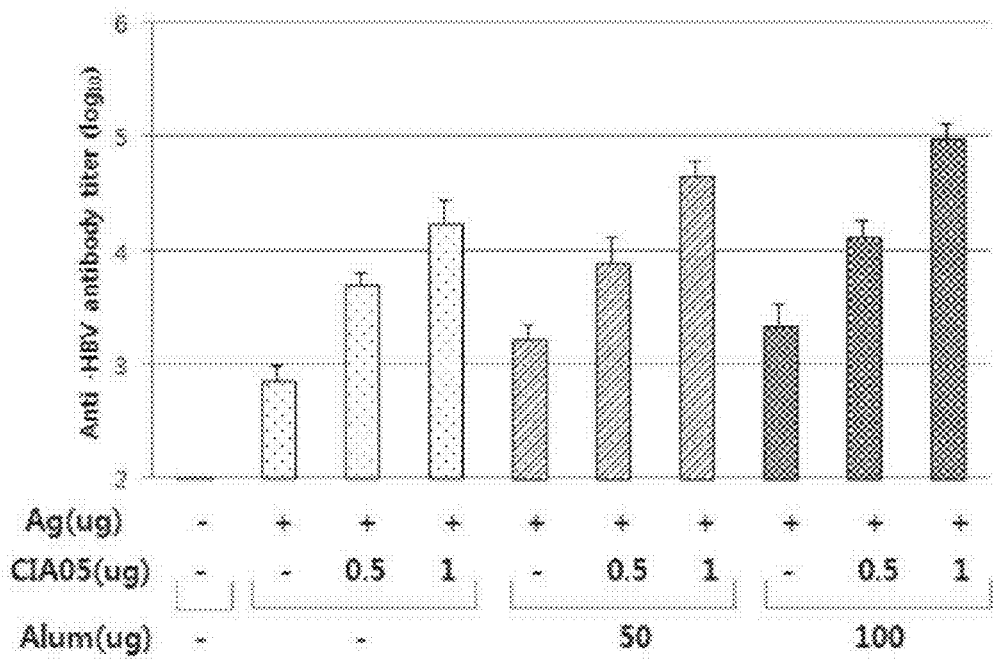
FIG. 5 is results of efficacy analysis on the present vaccine to HBV (Hepatitis B virus).

As a result, the production of HBsAg antigen-specific antibody in the Alum group was increased by approximately 2 times (50 μg of Alum) or approximately 4 times (100 μg of Alum) as compared to the antigen alone group. Moreover, the production of HBsAg antigen-specific antibody in the CIA05 group was increased by approximately 8 times (0.5 μg of CIA05) or approximately 16 times (1.0 μg of CIA05) as compared to the antigen alone group (FIG. 5). In addition, where CIA05 was used, the production level of HBsAg antigen-specific antibody was remarkably increased in a dose-dependent manner, indicating that CIA05 is a very suitable adjuvant for HBsAg antigen. Meanwhile, where the adjuvant CIA05 and Alum were used together, the production level of HBsAg antigen-specific antibody was increased by approximately 2 times (50 μg of Alum) or approximately 4 times (100 μg of Alum) as compared to the 0.5 μg of CIA05 alone group. Where the adjuvant CIA05 and Alum were used together, the production level of HBsAg antigen-specific antibody was increased by approximately 4 times (50 μg of Alum) or approximately 8 times (100 μg of Alum) as compared to the 1.0 μg of CIA05 alone group.

In conclusion, the present HBV vaccine including adjuvant CIA05, particularly, the HBV vaccine using the combination of HBsAg antigen and CIA05 has the excellent immunization efficacy, i.e., vaccine efficacy.

Example 7

Efficacy Analysis on the Present Vaccine to Hepatitis C Virus (HCV)

In order to verify efficacy of adjuvant CIA05 for HCV vaccine, commercial
HCV recombinant NS3 (Z00042, GenScrpt) was used as antigen.

Six-week old Balb/c mice were injected for 3-times at 1-week interval with 2 μg of NS3 antigen alone or the mixture including Alum or CIA05. At 1 week after the third injection, whole blood were collected from mouse and centrifuged to obtain serum, and NS3-specific antibody titer was measured with end-point ELISA method (Enzyme-Linked Immunosorbent Assay) as the same manner in Example 3.

Figure 6:
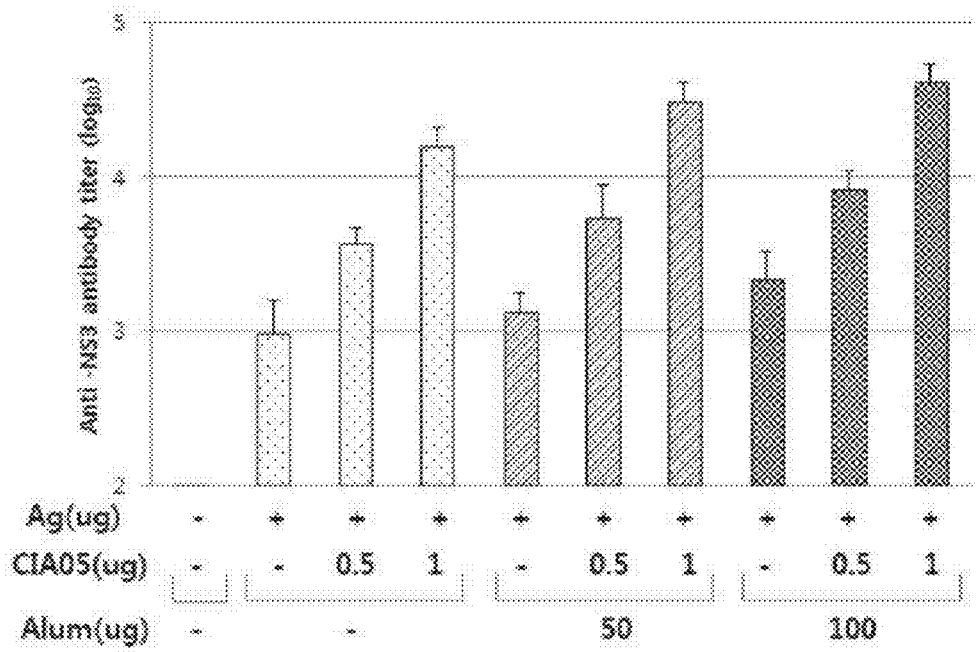
FIG. 6 is results of efficacy analysis on the present vaccine to HCV (Hepatitis C virus).

As a result, the production of NS3 antigen-specific antibody in the Alum group was increased by approximately 2 times (50 μg of Alum) or approximately 4 times (100 μg of Alum) as compared to the antigen alone group. Moreover, the production of NS3 antigen-specific antibody in the CIA05 group was increased by approximately 4 times (0.5 μg of CIA05) or approximately 16 times (1.0 μg of CIA05) as compared to the antigen alone group (FIG. 6). In addition, where CIA05 was used, the production level of NS3 antigen-specific antibody was remarkably increased in a dose-dependent manner, indicating that CIA05 is a very suitable adjuvant for NS3 antigen. Meanwhile, where the adjuvant CIA05 and Alum were used together, the production level of NS3 antigen-specific antibody was increased by approximately 2 times (50 μg of Alum) or approximately 4 times (100 μg of Alum) as compared to the 0.5 μg of CIA05 alone group. Where the adjuvant CIA05 and Alum were used together, the production level of NS3 antigen-specific antibody was increased by approximately 2 times (50 μg of Alum) or approximately 4 times (100 μg of Alum) as compared to the 1.0 μg of CIA05 alone group.

In conclusion, the present HCV vaccine including adjuvant CIA05, particularly, the HCV vaccine using the combination of NS3 antigen and CIA05 has the excellent immunization efficacy, i.e., vaccine efficacy.

Example 8

Efficacy Analysis on the Present Vaccine to HIV

In order to verify efficacy of adjuvant CIA05 for HIV vaccine, commercial HIV-1 envelope antigen (Env) (H9909, Sigma) was used as antigen. Six-week old Balb/c mice were injected for 3-times at 1-week interval with 2 μg of HIV-1 Env antigen alone or the mixture including Alum or CIA05. At 1 week after the third injection, whole blood were collected from mouse and centrifuged to obtain serum, and HIV-1 Env-specific antibody titer was measured with end-point ELISA method (Enzyme-Linked Immunosorbent Assay) as the same manner in Example 3.

Figure 7:
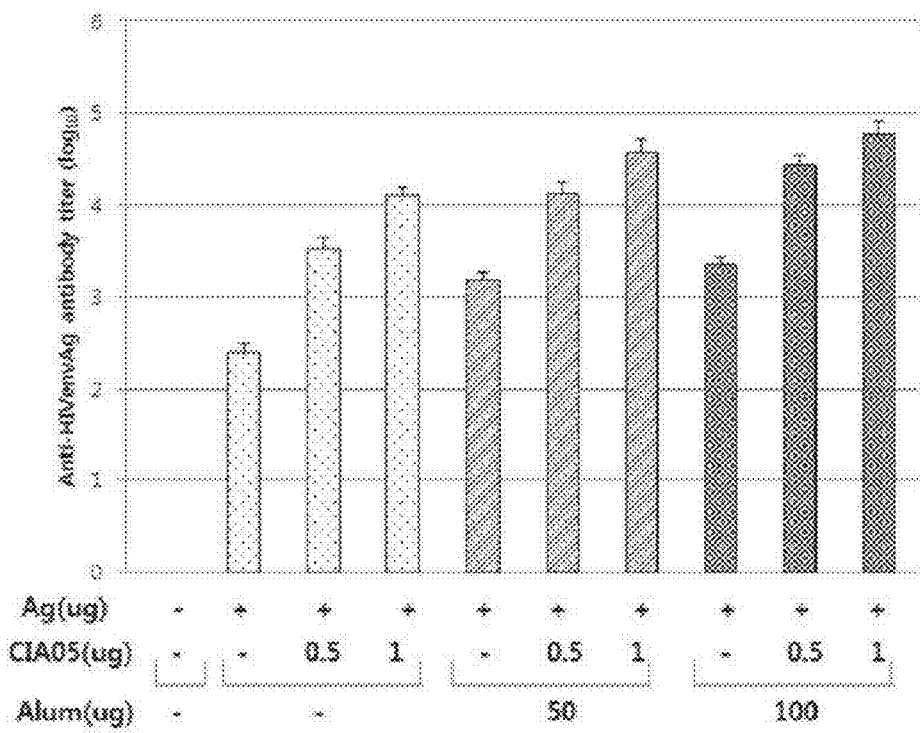
FIG. 7 is results of efficacy analysis on the present vaccine to HIV.

As a result, the production of HIV-1 Env antigen-specific antibody in the Alum group was increased by approximately 4 times (50 μg of Alum) or approximately 8 times (100 μg of Alum) as compared to the antigen alone group. Moreover, the production of HIV-1 Env antigen-specific antibody in the CIA05 group was increased by approximately 16 times (0.5 μg of CIA05) or approximately 64 times (1.0 μg of CIA05)

as compared to the antigen alone group (FIG. 7). In addition, where CIA05 was used, the production level of HIV-1 Env antigen-specific antibody was remarkably increased in a dose-dependent manner, indicating that CIA05 is a very suitable adjuvant for HIV-1 Env antigen. Meanwhile, where the adjuvant CIA05 and Alum were used together, the production level of HIV-1 Env antigen-specific antibody was increased by approximately 4 times (50 μg of Alum) or approximately 8 times (100 μg of Alum) as compared to the 0.5 μg of CIA05 alone group. Where the adjuvant CIA05 and Alum were used together, the production level of HIV-1 Env antigen-specific antibody was increased by approximately 4 times (50 μg of Alum) or approximately 8 times (100 μg of Alum) as compared to the 1.0 μg of CIA05 alone group.

In conclusion, the present HIV vaccine including adjuvant CIA05, particularly, the HIV vaccine using the combination of HIV-1 Env antigen and CIA05 has the excellent immunization efficacy, i.e., vaccine efficacy.

Example 9

Efficacy Analysis on the Present Vaccine to Influenza

In order to verify efficacy of adjuvant CIA05 for influenza vaccine, commercial HA subunit (C J Co., Incheon, Korea) obtained from 3 types of influenza virus strains was used as antigen. The 3 types of influenza virus strains are A/New Caledonia/20/99 (H1N1), A/Panama/2007/99 (H3N2) and B/Shangdong/7/97. Six-week old Balb/c mice were injected for 2-times at 4-week interval with 1.5 μg of HA subunit antigen alone or the mixture including Alum or CIA05. At 4 days after the second injection, whole blood were collected from mouse and centrifuged to obtain serum, and HA subunit-specific antibody titer was measured with end-point ELISA method (Enzyme-Linked Immunosorbent Assay) as the same manner in Example 3.

Figure 8:
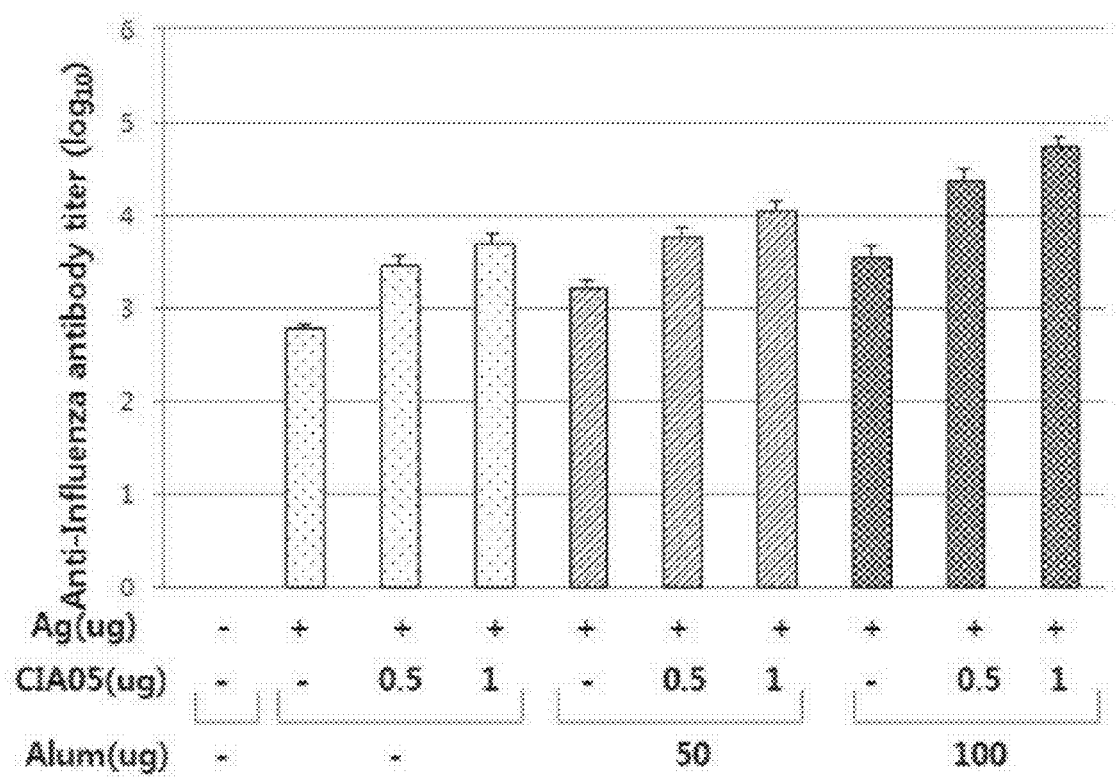
FIG. 8 is results of efficacy analysis on the present vaccine to influenza.

As a result, the production of HA subunit antigen-specific antibody in the Alum group was increased by approximately 2 times (50 μg of Alum) or approximately 4 times (100 μg of Alum) as compared to the antigen alone group. Moreover, the production of HA subunit antigen-specific antibody in the CIA05 group was increased by approximately 4 times (0.5 μg of CIA05) or approximately 8 times (1.0 μg of CIA05) as compared to the antigen alone group (FIG. 8). In addition, where CIA05 was used, the production level of HA subunit antigen-specific antibody was remarkably increased in a dose-dependent manner, indicating that CIA05 is a very suitable adjuvant for HA subunit antigen. Meanwhile, where the adjuvant CIA05 and Alum were used together, the production level of HA subunit antigen-specific antibody was increased by approximately 2 times (50 μg of Alum) or approximately 8 times (100 μg of Alum) as compared to the 0.5 μg of CIA05 alone group. Where the adjuvant CIA05 and Alum were used together, the production level of HA subunit antigen-specific antibody was increased by approximately 2 times (50 μg of Alum) or approximately 8 times (100 μg of Alum) as compared to the 1.0 μg of CIA05 alone group.

In conclusion, the present influenza vaccine including adjuvant CIA05, particularly, the influenza vaccine using the combination of HA subunit antigen and CIA05 has the excellent immunization efficacy, i.e., vaccine efficacy.

Example 10

Efficacy Analysis on the Present Vaccine to HSV-2 (Herpes Simplex Virus Type 2)

In order to verify efficacy of adjuvant CIA05 for HSV-2 vaccine, glycoprotein gD and gB of HSV-2 were used as antigen. Glycosylation in 2 types of the antigens were important so that 2 types of the antigens were expressed in mammalian cells (CHO cell line) and purified (Boucher et al., Detection of antibodies to herpes simplex virus type 2 with a mammalian cell line expressing glycoprotein gG-2. *Clin. Diagn. Virol.* 1(1):29-38(1993)). Six-week old Balb/c mice were injected for 3-times at 1-week interval with the antigens (each 2 μg) alone or the mixture including Alum or CIA05. At 1 week after the third injection, whole blood were collected from mouse and centrifuged to obtain serum, and HSV-2 antigen gD- and gB-specific antibody titer were measured with end-point ELISA method (Enzyme-Linked Immunosorbent Assay) as the same manner in Example 3.

Figure 9A:
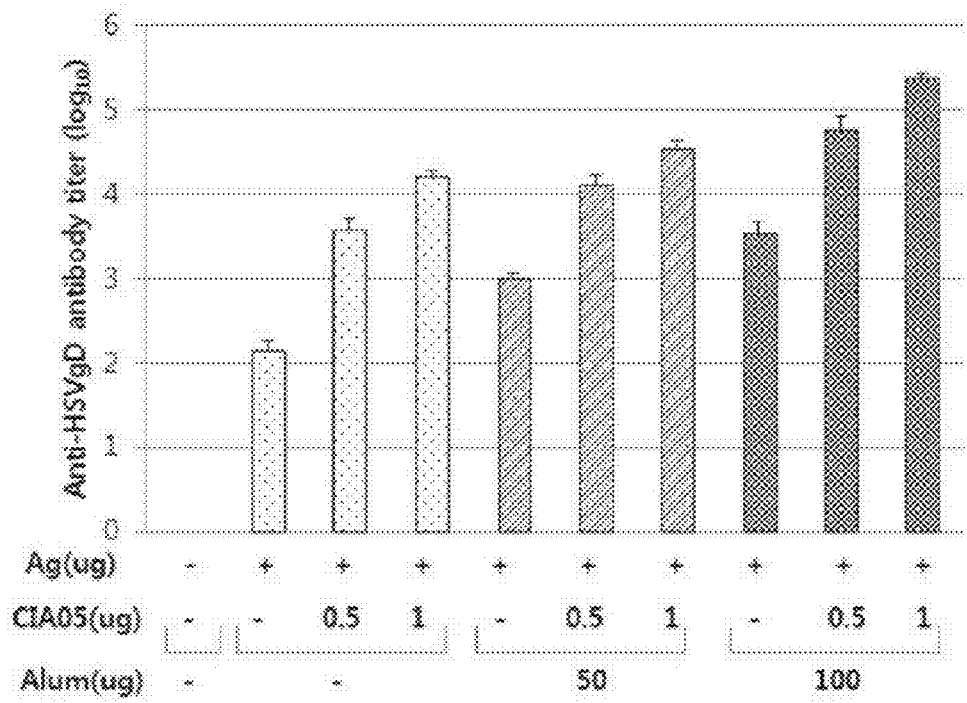
FIGS. 9a-b are results of efficacy analysis on the present vaccine to HSV-2 (Herpes simplex virus 2).

As a result, in case of gD antigen, the production of gD antigen-specific antibody in the Alum group was increased by approximately 8 times (50 μg of Alum) or approximately 32 times (100 μg of Alum) as compared to the antigen alone group. Moreover, the production of gD antigen-specific antibody in the CIA05 group was increased by approximately 24 times (0.5 μg of CIA05) or approximately 128 times (1.0 μg of CIA05) as compared to the antigen alone group (FIG. 9a). In addition, where CIA05 was used, the production level of gD antigen-specific antibody was remarkably increased in a dose-dependent manner, indicating that CIA05 is a very suitable adjuvant for gD antigen. Meanwhile, where the adjuvant CIA05 and Alum were used together, the production level of gD antigen-specific antibody was increased by approximately 4 times (50 μg of Alum) or approximately 16 times (100 μg of Alum) as compared to the 0.5 μg of CIA05 alone group. Where the adjuvant CIA05 and Alum were used together, the production level of gD antigen-specific antibody was increased by approximately 2 times (50 μg of Alum) or approximately 16 times (100 μg of Alum) as compared to the 1.0 μg of CIA05 alone group.

Figure 9B:
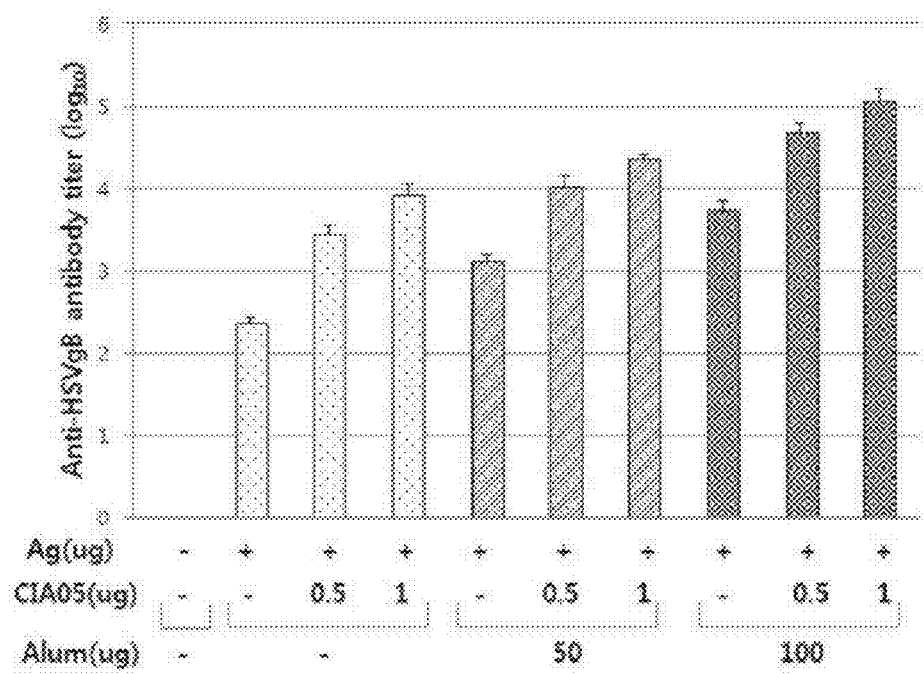

In case of gB antigen, the production of gB antigen-specific antibody in the Alum group was increased by approximately 8 times (50 μg of Alum) or approximately 32 times (100 μg of Alum) as compared to the antigen alone group. Moreover, the production of gB antigen-specific antibody in the CIA05 group was increased by approximately 16 times (0.5 μg of CIA05) or approximately 32 times (1.0 μg of CIA05) as compared to the antigen alone group (FIG. 9b). In addition, where CIA05 was used, the production level of gB antigen-specific antibody was remarkably increased in a dose-dependent manner, indicating that CIA05 is a very suitable adjuvant for gB antigen. Meanwhile, where the adjuvant CIA05 and Alum were used together, the production level of gB antigen-specific antibody was increased by approximately 4 times (50 μg of Alum) or approximately 16 times (100 μg of Alum) as compared to the 0.5 μg of CIA05 alone group. Where the adjuvant CIA05 and Alum were used together, the production level of gB antigen-specific antibody was increased by approximately 4 times (50 μg of Alum) or approximately 16 times (100 μg of Alum) as compared to the 1.0 μg of CIA05 alone group.

Figure 9C:
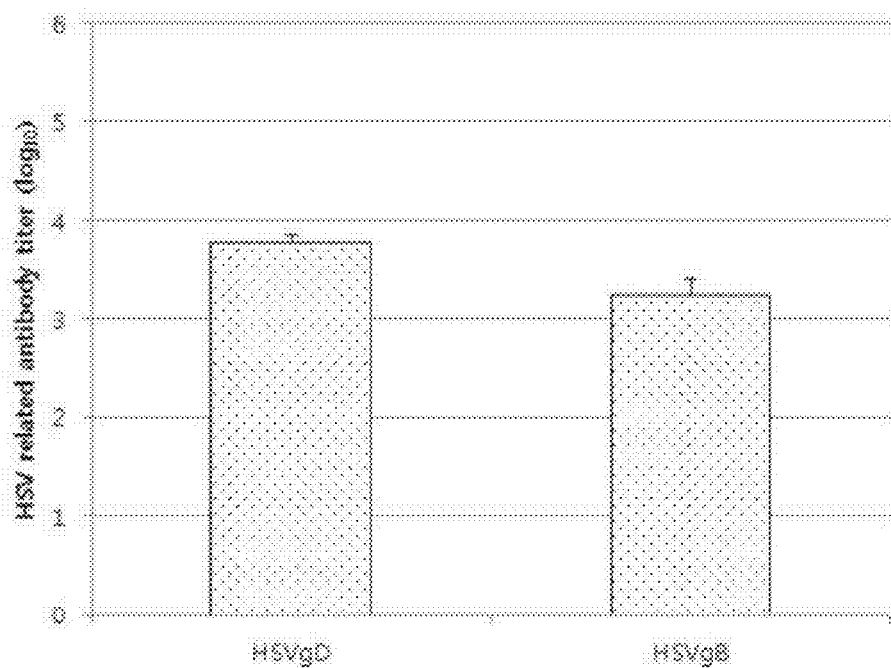
FIG. 9c is results of comparison on immunostimulatory effect of gD and gB. CIA05 (0.5 μg) and antigens (each 2 μg) were used.

The test was conducted to select the best antigen for immunostimulatory effect among HSV-2 antigens (FIG. 9c). As a result, the best antigen for immunostimulatory effect was gD. Therefore, it would be determined that the most appreciate antigen for the present CIA05 was gD.

In conclusion, the present HSV-2 vaccine including adjuvant CIA05, particularly, the HSV-2 vaccine using the combination of gD antigen and CIA05 has the excellent immunization efficacy, i.e., vaccine efficacy.

Example 11

Efficacy Analysis on the Present Vaccine to Hib (*Haemophilus Influenzae* Type b)

In order to verify efficacy of adjuvant CIA05 for Hib vaccine, commercial ActHIB (*Haemophilus* b conjugate Vaccine, Tetanus Toxoid Conjugate, Sanofi Pasteur S A) was used as antigen. Balb/c mice were injected for 2-times at 2-week interval with the antigen alone or the mixture including Alum or CIA05. At 1 week after the second injection, whole blood were collected from mouse and centrifuged to obtain serum, and Hib-specific antibody titer was measured with end-point ELISA method (Enzyme-Linked Immunosorbent Assay) as the same manner in Example 3.

Figure 10:
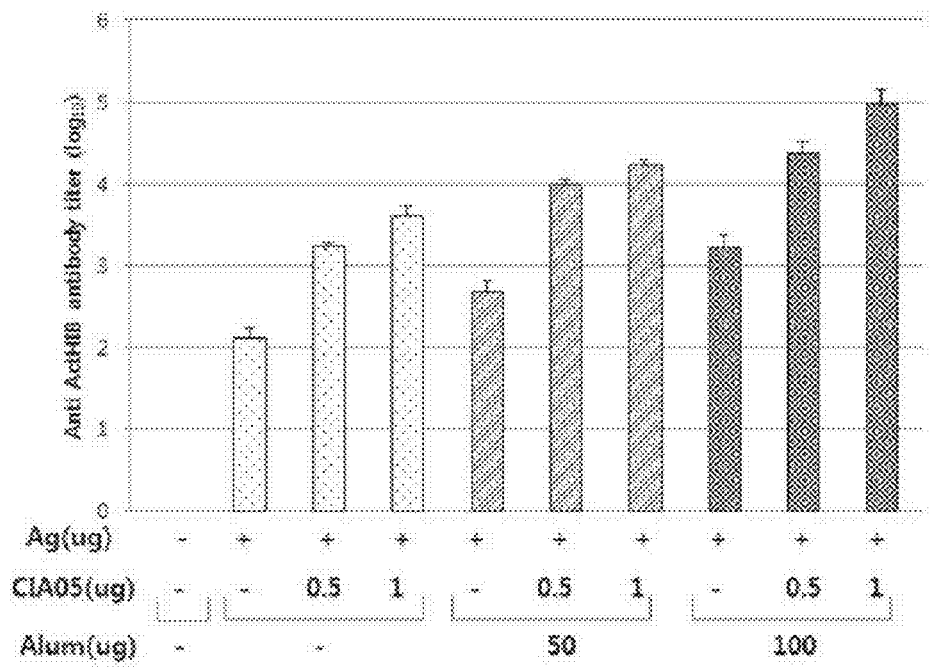
FIG. 10 is results of efficacy analysis on the present vaccine to Hib (*Haemophilus influenzae* type b).

As a result, the production of ActHIB antigen-specific antibody in the Alum group was increased by approximately 4 times (50 μg of Alum) or approximately 16 times (100 μg of Alum) as compared to the antigen alone group. Moreover, the production of Hib antigen-specific antibody in the CIAOS group was increased by approximately 16 times (0.5 μg of CIA05) or approximately 32 times (1.0 μg of CIA05) as compared to the antigen alone group (FIG. 10). In addition, where CIA05 was used, the production level of ActHIB antigen-specific antibody was remarkably increased in a dose-dependent manner, indicating that CIA05 is a very suitable adjuvant for ActHIB antigen. Meanwhile, where the adjuvant CIA05 and Alum were used together, the production level of ActHIB antigen-specific antibody was increased by approximately 8 times (50 μg of Alum) or approximately 16 times (100 μg of Alum) as compared to the 0.5 μg of CIA05 alone group. Where the adjuvant CIA05 and Alum were used together, the production level of ActHIB antigen-specific antibody was increased by approximately 4 times (50 μg of Alum) or approximately 24 times (100 μg of Alum) as compared to the 1.0 μg of CIAOS alone group.

In conclusion, the present Hib vaccine including adjuvant CIA05, particularly, the Hib vaccine using the combination of ActHIB and CIAOS has the excellent immunization efficacy, i.e., vaccine efficacy.

Example 12

Efficacy Analysis on the Present Vaccine to *Neisseria Meningitidis*

In order to verify efficacy of adjuvant CIA05 for *Neisseria meningitidis* vaccine, proteosome isolated from attenuated *Neisseria meningitidis* was used as antigen (Lowell et al., Proteosome-lipopeptide vaccines: enhancement of immunogenicity for malaria CS peptides. *Science,* 240:800-802 (1980)). Six-week old Balb/c mice were injected for 2-times at 2-week interval with the antigen alone or the mixture including Alum or CIA05. At 1 week after the second injection, whole blood were collected from mouse and centrifuged to obtain serum, and *Neisseria meningitidis* proteosome-specific antibody titer was measured with end-point ELISA method (Enzyme-Linked Immunosorbent Assay) as the same manner in Example 3.

Figure 11:
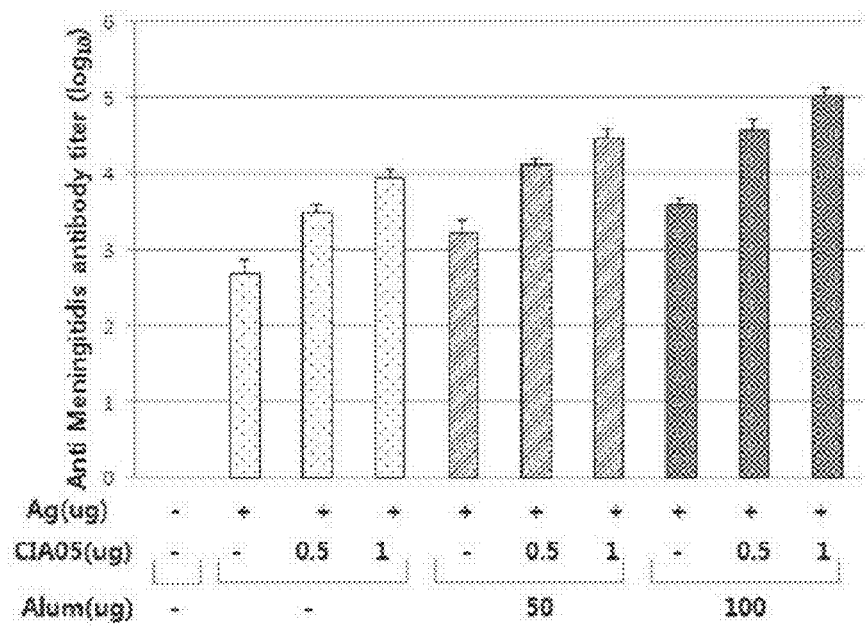
FIG. 11 is results of efficacy analysis on the present vaccine to *Neisseria meningitidis*.

As a result, the production of *Neisseria meningitidis* proteosome antigen-specific antibody in the Alum group was increased by approximately 4 times (50 μg of Alum) or approximately 8 times (100 μg of Alum) as compared to the antigen alone group. Moreover, the production of *Neisseria meningitidis* proteosome antigen-specific antibody in the CIA05 group was increased by approximately 8 times (0.5 μg of CIA05) or approximately 16 times (1.0 μg of CIA05) as compared to the antigen alone group (FIG. 11). In addition, where CIA05 was used, the production level of *Neisseria meningitidis* proteosome antigen-specific antibody was remarkably increased in a dose-dependent manner, indicating that CIA05 is a very suitable adjuvant for *Neisseria meningitidis* proteosome antigen. Meanwhile, where the adjuvant CIA05 and Alum were used together, the production level of *Neisseria meningitidis* proteosome antigen-specific antibody was increased by approximately 4 times (50 μg of Alum) or approximately 16 times (100 μg of Alum) as compared to the 0.5 μg of CIA05 alone group. Where the adjuvant CIA05 and Alum were used together, the production level of HA subunit antigen-specific antibody was increased by approximately 4 times (50 μg of Alum) or approximately 16 times (100 μg of Alum) as compared to the 1.0 μg of CIA05 alone group.

In conclusion, the present *Neisseria meningitidis* vaccine including adjuvant CIA05, particularly, the *Neisseria meningitidis* vaccine using the combination of *Neisseria meningitidis* proteosome and CIA05 has the excellent immunization efficacy, i.e., vaccine efficacy.

Example 13

Efficacy Analysis on the Present Vaccine to Diphtheria, Pertussis, Tetanus (DPT)

DPT is a vaccine for preventing diseases caused by diphtheria, pertussis and tetanus. Vaccine to these diseases In order to verify efficacy of adjuvant CIA05 for vaccine to these diseases, commercial Diphtheria toxin (D0564, Sigma) derived from *Corynebacterium diphtheria* was used as diphtheria antigen. Commercial Pertusis toxin (P7208, Sigma) derived from *Bordetella pertussispertussis* was used as pertussis antigen. Commercial Tetanus toxin (T3194, Sigma) derived from *Clostridium tetani* was used as tetanus antigen. Six-week old Balb/c mice were injected for 2-times at 2-week interval with the antigens (each 2 μg) alone or the mixture including Alum or CIA05. At 1 week after the second injection, whole blood were collected from mouse and centrifuged to obtain serum, and each toxin-specific antibody titer was measured with end-point ELISA method (Enzyme-Linked Immunosorbent Assay) as the same manner in Example 3.

Figure 12A:
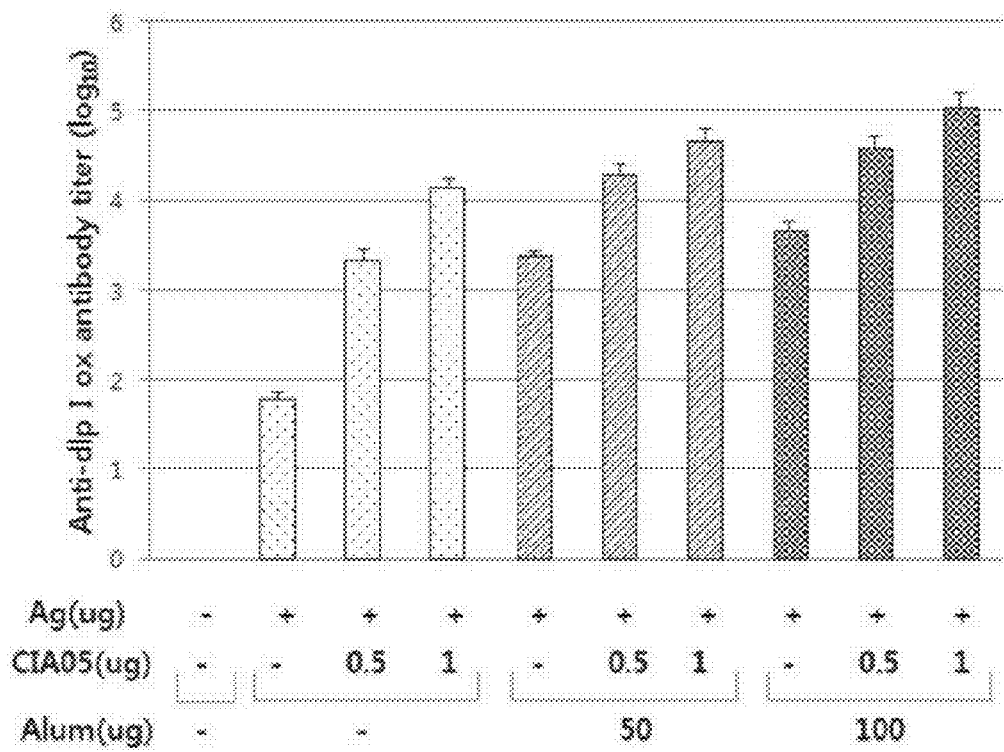
FIGS. 12a-c are results of efficacy analysis on the present vaccine to DPT.

As a result, in case of Diphtheria toxin antigen, the production of Diphtheria toxin antigen-specific antibody in the Alum group was increased by approximately 32 times (50 μg of Alum) or approximately 64 times (100 μg of Alum) as compared to the antigen alone group. Moreover, the production of Diphtheria toxin antigen-specific antibody in the CIA05 group was increased by approximately 32 times (0.5 μg of CIA05) or approximately 128 times (1.0 μg of CIA05) as compared to the antigen alone group (FIG. 12a). In addition, where CIA05 was used, the production level of Diphtheria toxin antigen-specific antibody was remarkably increased in a dose-dependent manner, indicating that CIA05 is a very suitable adjuvant for Diphtheria toxin antigen. Meanwhile, where the adjuvant CIA05 and Alum were used together, the production level of Diphtheria toxin antigen-specific antibody was increased by approximately 8 times (50 µg of Alum) or approximately 16 times (100 µg of Alum) as compared to the 0.5 µg of CIA05 alone group. Where the adjuvant CIA05 and Alum were used together, the production level of Diphtheria toxin antigen-specific antibody was increased by approximately 4 times (50 µg of Alum) or approximately 8 times (100 µg of Alum) as compared to the 1.0 µg of CIA05 alone group.

Figure 12B:
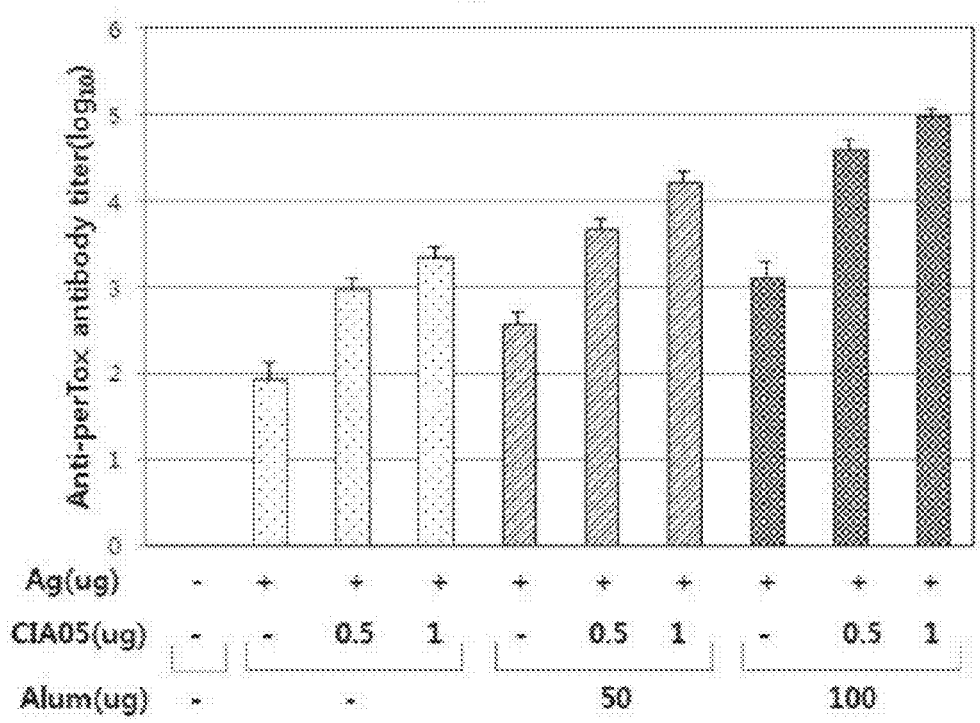
Figure 12C:
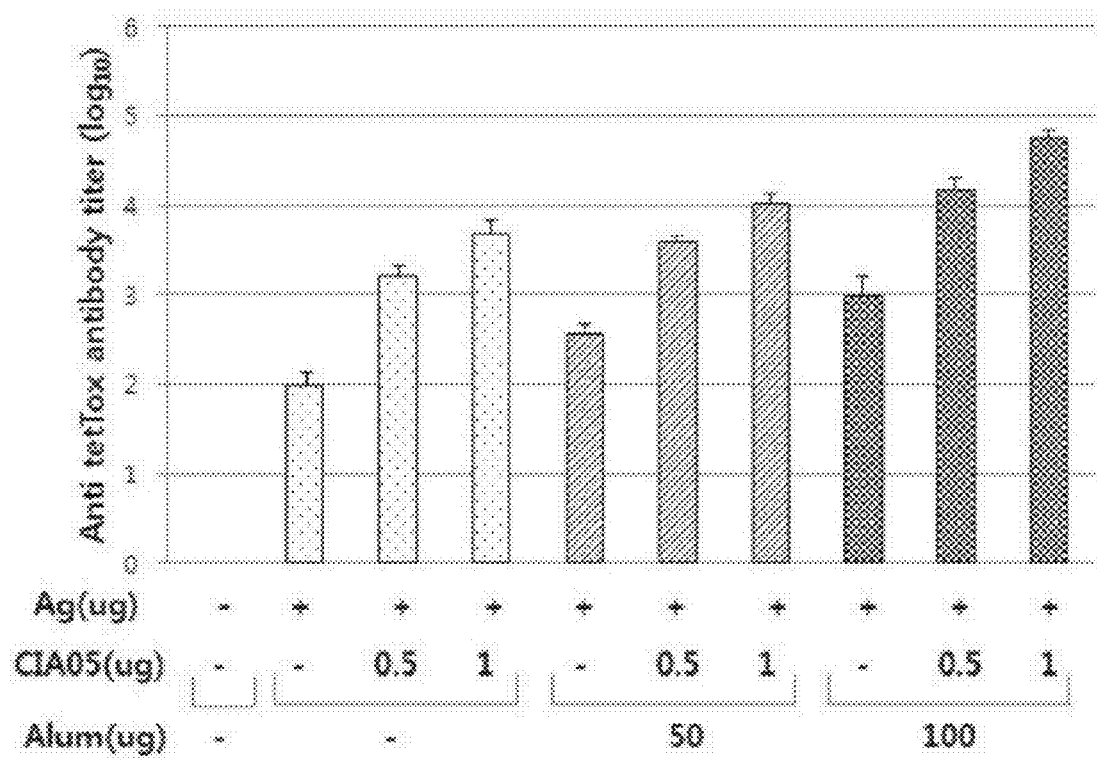

In case of Pertusis toxin antigen, the production of Pertusis toxin antigen-specific antibody in the Alum group was increased by approximately 4 times (50 µg of Alum) or approximately 16 times (100 µg of Alum) as compared to the antigen alone group. Moreover, the production of Pertusis toxin antigen-specific antibody in the CIA05 group was increased by approximately 16 times (0.5 µg of CIA05) or approximately 24 times (1.0 µg of CIA05) as compared to the antigen alone group (FIG. 12b). In addition, where CIA05 was used, the production level of Pertusis toxin antigen-specific antibody was remarkably increased in a dose-dependent manner, indicating that CIA05 is a very suitable adjuvant for Diphtheria toxin antigen. Meanwhile, where the adjuvant CIA05 and Alum were used together, the production level of Pertusis toxin antigen-specific antibody was increased by approximately 4 times (50 µg of Alum) or approximately 32 times (100 µg of Alum) as compared to the 0.5 µg of CIA05 alone group. Where the adjuvant CIA05 and Alum were used together, the production level of Pertusis toxin antigen-specific antibody was increased by approximately 8 times (50 µg of Alum) or approximately 32 times (100 µg of Alum) as compared to the 1.0 µg of CIA05 alone group.

In case of Tetanus toxin antigen, the production of Tetanus toxin antigen-specific antibody in the Alum group was increased by approximately 4 times (50 µg of Alum) or approximately 8 times (100 µg of Alum) as compared to the antigen alone group. Moreover, the production of Tetanus toxin antigen-specific antibody in the CIA05 group was increased by approximately 16 times (0.5 µg of CIA05) or approximately 32 times (1.0 µg of CIA05) as compared to the antigen alone group (FIG. 12b). In addition, where CIA05 was used, the production level of Tetanus toxin antigen-specific antibody was remarkably increased in a dose-dependent manner, indicating that CIA05 is a very suitable adjuvant for Diphtheria toxin antigen. Meanwhile, where the adjuvant CIA05 and Alum were used together, the production level of Tetanus toxin antigen-specific antibody was increased by approximately 4 times (50 µg of Alum) or approximately 8 times (100 µg of Alum) as compared to the 0.5 µg of CIA05 alone group. Where the adjuvant CIA05 and Alum were used together, the production level of Tetanus toxin antigen-specific antibody was increased by approximately 4 times (50 µg of Alum) or approximately 8 times (100 µg of Alum) as compared to the 1.0 µg of CIA05 alone group.

Figure 12D:
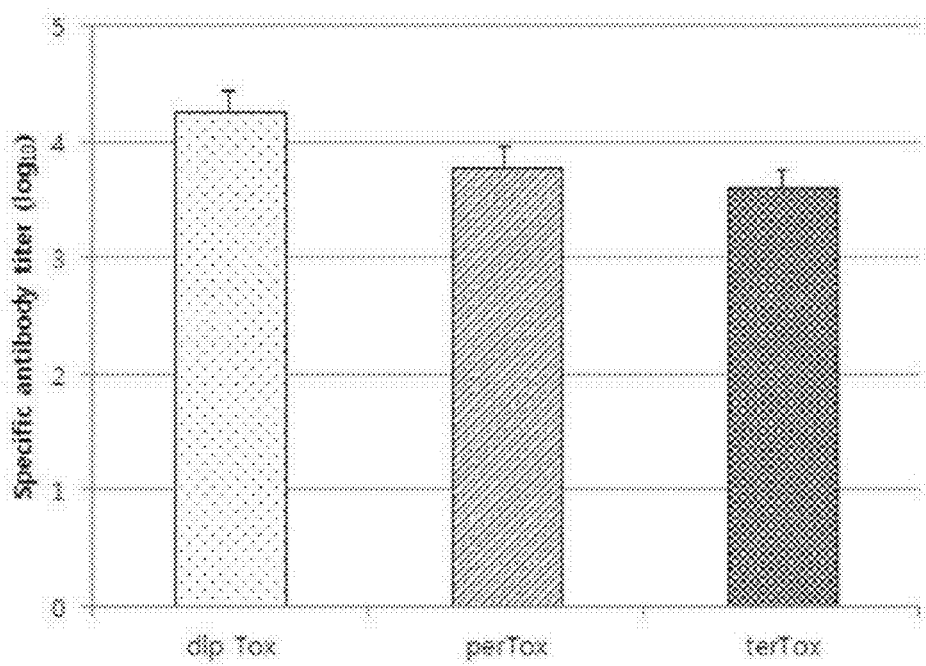
FIG. 12d is results of comparison on immunostimulatory effect of Diphtheria toxin, Pertusis toxin and Tetanus toxin. CIA05 (0.5 μg) and antigens (each 2 μg) were used.

The test was conducted to select the best antigen for immunostimulatory effect among DPT antigens (FIG. 12d). As a result, the best antigen for immunostimulatory effect was Diphtheria toxin, Pertusis toxin and Tetanus toxin in order. Therefore, it would be determined that the most appreciate antigen for the present CIA05 was Diphtheria toxin.

In conclusion, the present DPT vaccine including adjuvant CIA05, particularly, the DPT vaccine using the combination of Diphtheria toxin and CIA05 has the excellent immunization efficacy, i.e., vaccine efficacy.

Example 14

Efficacy Analysis on the Present Vaccine to Varicella

In order to verify efficacy of adjuvant CIA05 for varicella vaccine, 1VIA Suduvax strain (1VIA Suduvax inj, GREEN CROSS CORP.) was used as antigen. The Suduvax strain is a varicella vaccine in the form of live attenuated varicella. Six-week old Balb/c mice were injected for 2-times at 2-week interval with the antigen alone or the mixture including Alum or CIA05. At 1 week after the second injection, whole blood were collected from mouse and centrifuged to obtain serum, and Suduvax strain-specific antibody titer was measured with end-point ELISA method (Enzyme-Linked Immunosorbent Assay) as the same manner in Example 3.

Figure 13:
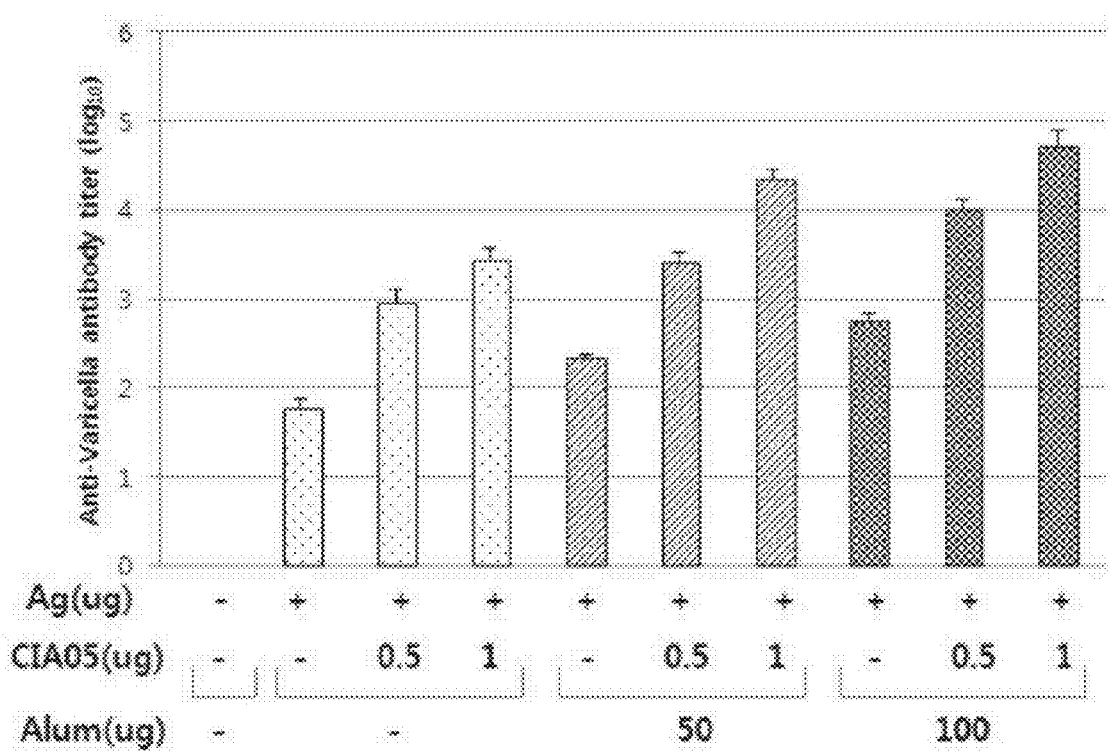
FIG. 13 is results of efficacy analysis on the present vaccine to Varicella.

As a result, the production of Suduvax strain antigen-specific antibody in the Alum group was increased by approximately 4 times (50 µg of Alum) or approximately 8 times (100 µg of Alum) as compared to the antigen alone group. Moreover, the production of *Neisseria meningitidis* proteosome antigen-specific antibody in the CIA05 group was increased by approximately 16 times (0.5 µg of CIA05) or approximately 64 times (1.0 µg of CIA05) as compared to the antigen alone group (FIG. 13). In addition, where CIA05 was used, the production level of Suduvax strain antigen-specific antibody was remarkably increased in a dose-dependent manner, indicating that CIA05 is a very suitable adjuvant for Suduvax strain antigen (attenuated varicella). Meanwhile, where the adjuvant CIA05 and Alum were used together, the production level of *Neisseria meningitidis* proteosome antigen-specific antibody was increased by approximately 4 times (50 µg of Alum) or approximately 8 times (100 µg of Alum) as compared to the 0.5 µg of CIA05 alone group. Where the adjuvant CIA05 and Alum were used together, the production level of HA subunit antigen-specific antibody was increased by approximately 4 times (50 µg of Alum) or approximately 32 times (100 µg of Alum) as compared to the 1.0 µg of CIA05 alone group.

In conclusion, the present varicella vaccine including adjuvant CIA05, particularly, the varicella vaccine using the combination of attenuated varicella and CIA05 has the excellent immunization efficacy, i.e., vaccine efficacy.

Example 15

Efficacy Analysis of CIA05 for Maturation of Dendritic Cells

Isolation of Human MDDCs (Monocyte-Derived DC Cells) and Mouse BMDC (Bone Marrow DCs)

Approximately 80 ml of blood from healthy human donors was collected and isolated peripheral blood mononuclear cells (PBMCs) with Ficoll-Paque™ gradient separation method. Monocytes were isolated from PBMCs using anti-CD14 microbeads (MACS system), seeded at $1 \times 10^8$ cells/ml in a 24-well plate with RPMI medium contained 10% FBS, IL-4 and GM-CSF and cultured to obtain human MDDCs. Bone marrow cells were isolated from male BALB/c mouse and cultured with medium contained IL-4 and GM-CSF for 6 days to obtain BMDCs. Then, at 7 days, CD11c$^+$ cells were isolated using anti-CD11c-coated magnetic beads.

Analysis on Expression Increase of Surface Marker of DCs (Dendritic Cells) by Adjuvant CIA05

Figure 14A:
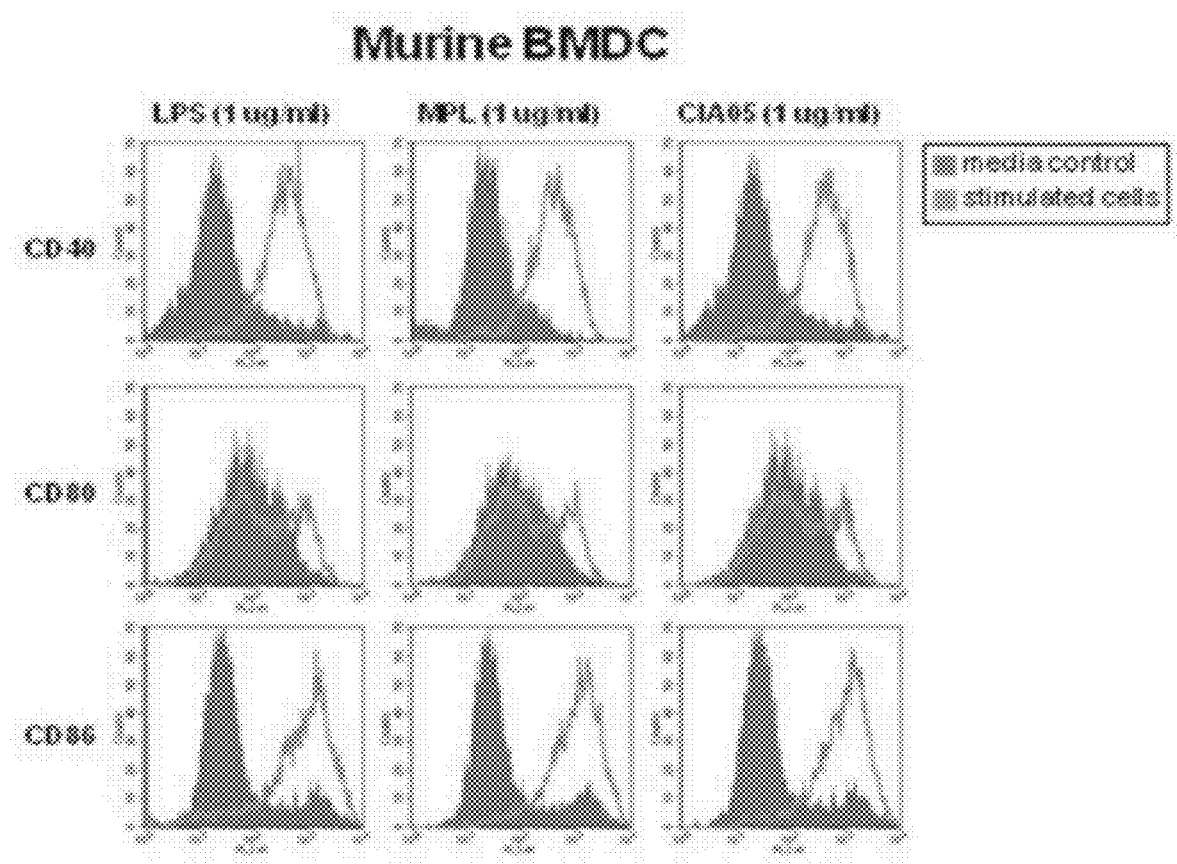
FIG. 14a is results of efficacy analysis on CIA05 (the adjuvant prepared in Example 1) for maturation of dendritic cells in mouse BMDC (Bone marrow DCs).
Figure 14B:
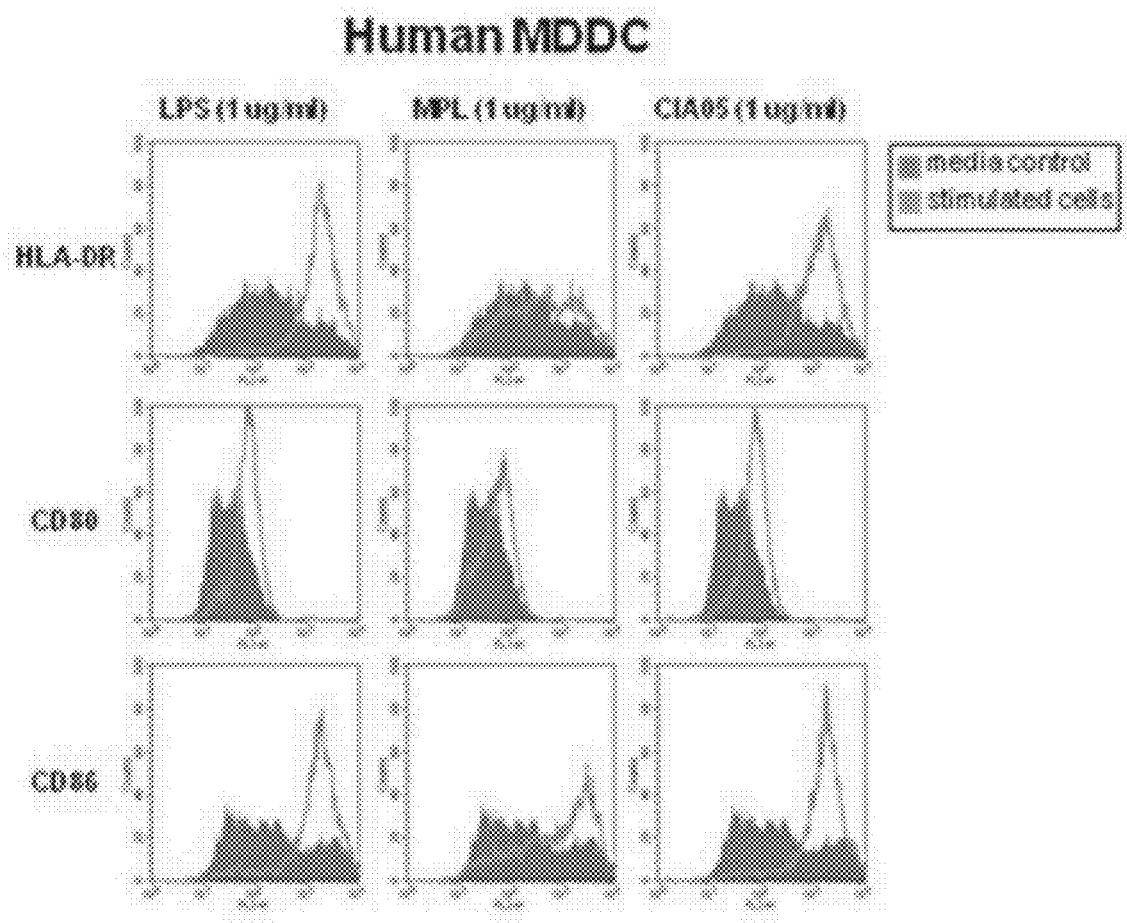
FIG. 14b is results of efficacy analysis on CIA05 (the adjuvant prepared in Example 1) for maturation of dendritic cells in human MDDCs (Monocyte-derived DC cells).

Human MDDCs (Monocyte-derived DC cells) and mouse BMDC (Bone marrow DCs) were isolated with the method described above, treated respectively with LPS, MPL and CIA05 with 1 µg/ml of concentration and incubated at 37° C. for 24 hrs. After incubation, CD40, CD80 and CD86 were verified in mouse BMDCs surface, and HLA-DR, CD80 and CD86 were verified in human MDDCs by flow cytometry, respectively. In mouse BMDCs, it would be determined that DCs surface marker CD40, CD80 and CD86 were expressed with similar distribution in all of LPS, MPL and CIA05 (FIG. 14a). However, in human MDDCs, it would be determined that MDDCs surface marker HLA-DR, CD80 and CD86 in CIA05 were more highly expressed than that in the MPL which has been widely used as vaccine adjuvant (FIG. 14b). It is indicated that efficacy of MPL is maintained with level of LPS in mouse, however, it is limited in human. Therefore, CIA05 may solve these problems.

In conclusion, adjuvant CIA05 acts to increase considerably immunization efficacy, i.e., vaccine efficacy, and particularly, it has the excellent effect for maturation of human dendritic cells.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for inducing immunity to an antigen in a subject comprising administering to the subject a pharmaceutically effective amount of a vaccine composition comprising: (a) a pathogen-derived antigen selected from a group consisting of influenza virus antigen, *Mycobacterium tuberculosis* antigen, *Bacillus anthracis* antigen, Varicella-zoster virus antigen which is live attenuated Varicella-zoster virus, inactivated attenuated Varicella-zoster virus, gpI or gpII, HAV (Hepatitis A virus) antigen, HCV (Hepatitis C virus) antigen, HIV (human immunodeficiency virus) antigen, HSV (Herpes simplex virus) antigen, Hib (*Haemophilus influenzae* type b) antigen, *Neisseria meningitidis* antigen, *Corynebacterium diphtheria* antigen, *Bordetella pertussis* antigen and *Clostridium tetani* antigen; (b) a deacylated non-toxic LOS (Lipooligosaccharide) having a molecular weight in a range of 2,000-4,000Da, obtained by deacylation of lipid A of lipopolysaccharide isolated from *Escherichia coli*; and (c) a pharmaceutically acceptable carrier, with the proviso that the vaccine composition does not include an oligodeoxynucleotide (ODN) as an adjuvant.

2. The method according to claim 1, wherein *Mycobacterium tuberculosis* antigen is at least one antigen selected from a group consisting of 65 kD heat shock protein (HSP65), antigen 85A (Ag85A), antigen 85B, antigen 85C, ESAT-6, Des protein, MPT32, MPT51, MPT63, MPT64, HspX and Phosphate binding protein 1.

3. The method according to claim 2, wherein *Mycobacterium tuberculosis* antigen is at least one antigen selected from a group consisting of antigen 85A (Ag85A), ESAT-6, HspX and Phosphate binding protein 1.

4. The method according to claim 1, wherein influenza virus antigen is envelope glycoprotein HA or NA.

5. The method according to claim 4, wherein influenza virus antigen is envelope glycoprotein HA.

6. The method according to claim 1, wherein the non-toxic LOS is detoxificated by deacylation of lipid A via alkaline treatment to LPS (lipopolysaccharide).

7. The method according to claim 1, wherein the pharmaceutical composition further comprises an immunoadjuvant which is: a Group II element selected from the group consisting of Mg, Ca, Sr, Ba and Ra; a Group IV element selected from the group consisting of Ti, Zr, Hf and Rf; or an aluminium salt or a hydrate thereof.

* * * * *